United States Patent
Schultz et al.

(10) Patent No.: US 11,772,956 B2
(45) Date of Patent: Oct. 3, 2023

(54) METHOD AND APPARATUS FOR LIMITING ACIDIC CORROSION AND CONTAMINATION IN FUEL DELIVERY SYSTEMS

(71) Applicant: FRANKLIN FUELING SYSTEMS, LLC, Madison, WI (US)

(72) Inventors: Nicholas Schultz, Verona, WI (US); James Novak, Evansville, WI (US); Bill Nelson, Lake Mills, WI (US); Randall Boucher, Saco, ME (US); Martin Turnidge, Saco, ME (US); George Risch, South Portland, ME (US); Todd Breuer, McFarland, WI (US)

(73) Assignee: FRANKLIN FUELING SYSTEMS, LLC, Madison, WI (US)

( * ) Notice: Subject to any disclaimer, the term of this patent is extended or adjusted under 35 U.S.C. 154(b) by 0 days.

(21) Appl. No.: 17/832,794

(22) Filed: Jun. 6, 2022

(65) Prior Publication Data
US 2022/0298002 A1  Sep. 22, 2022

Related U.S. Application Data

(62) Division of application No. 15/914,535, filed on Mar. 7, 2018, now Pat. No. 11,352,248.

(Continued)

(51) Int. Cl.
*B67D 7/76* (2010.01)
*B01D 17/04* (2006.01)
(Continued)

(52) U.S. Cl.
CPC ........... *B67D 7/766* (2013.01); *B01D 17/045* (2013.01); *B01D 35/02* (2013.01); *B01D 36/005* (2013.01);
(Continued)

(58) Field of Classification Search
CPC ... B67D 7/32; B67D 7/62; B67D 7/68; B67D 7/76; B67D 7/725; B67D 7/766; B67D 7/78; B01D 35/02; B01D 36/008
See application file for complete search history.

(56) References Cited

U.S. PATENT DOCUMENTS 1,780,679 A  11/1930  Jennings
2,442,379 A   6/1948  Samiran
(Continued)

FOREIGN PATENT DOCUMENTS

CN       2665230 Y   12/2004
CN     104797996 A    7/2015
(Continued)

OTHER PUBLICATIONS

"Biochemistry of Acetic Bacteria", available online at https://people.ok.ubc.ca/neggers/Chem422A/Biochemistry%20OF%20ACETIC%20ACID%20BACTERIA.pdf, at least as early as Mar. 2012.
(Continued)

*Primary Examiner* — Timothy L Maust
(74) *Attorney, Agent, or Firm* — Faegre Drinker Biddle & Reath LLP

(57) ABSTRACT

A method and apparatus are provided for controlling a fuel delivery system to limit acidic corrosion. An exemplary control system includes a controller, at least one monitor, an output, and a remediation system. The monitor of the control system may collect and analyze data indicative of a corrosive environment in the fuel delivery system. The output of the control system may automatically warn an operator of the fueling station of the corrosive environment so that the operator can take preventative or corrective action. The remediation system of the control system may take at least one corrective action to remediate the corrosive environment in the fuel delivery system.

12 Claims, 17 Drawing Sheets

Related U.S. Application Data

(60) Provisional application No. 62/563,596, filed on Sep. 26, 2017, provisional application No. 62/520,891, filed on Jun. 16, 2017, provisional application No. 62/509,506, filed on May 22, 2017, provisional application No. 62/468,033, filed on Mar. 7, 2017.

(51) Int. Cl.

| | | |
|---|---|---|
| *B01D 36/00* | (2006.01) | |
| *B67D 7/32* | (2010.01) | |
| *G01N 33/28* | (2006.01) | |
| *B67D 7/78* | (2010.01) | |
| *F02M 37/44* | (2019.01) | |
| *B67D 7/68* | (2010.01) | |
| *B67D 7/72* | (2010.01) | |
| *B01D 35/02* | (2006.01) | |
| *F02M 37/28* | (2019.01) | |
| *F02M 37/32* | (2019.01) | |
| *B67D 7/62* | (2010.01) | |

(52) U.S. Cl.
CPC ............ *B01D 36/006* (2013.01); *B67D 7/32* (2013.01); *B67D 7/68* (2013.01); *B67D 7/725* (2013.01); *B67D 7/76* (2013.01); *B67D 7/78* (2013.01); *F02M 37/28* (2019.01); *F02M 37/32* (2019.01); *F02M 37/44* (2019.01); *G01N 33/2858* (2013.01); *B67D 7/3209* (2013.01); *B67D 7/62* (2013.01); *B67D 2007/329* (2013.01); *B67D 2210/0001* (2013.01)

(56) References Cited

U.S. PATENT DOCUMENTS

| | | |
|---|---|---|
| 2,853,149 A | 9/1958 | Gosselin |
| 2,960,106 A | 11/1960 | Dyer et al. |
| 3,246,144 A | 4/1966 | Beall et al. |
| 3,249,229 A | 5/1966 | Kasten |
| 3,591,050 A | 7/1971 | Kupersmith et al. |
| 3,661,262 A | 5/1972 | Sanders |
| 3,885,588 A | 5/1975 | Shotmeyer |
| 3,908,690 A | 9/1975 | Shotmeyer |
| 3,915,206 A | 10/1975 | Fowler et al. |
| 3,952,781 A | 4/1976 | Hiller et al. |
| 4,337,119 A | 6/1982 | Donahue |
| 4,620,669 A | 11/1986 | Polk |
| 4,639,164 A | 1/1987 | Pugnale et al. |
| 4,760,863 A | 8/1988 | Broer |
| 4,770,317 A | 9/1988 | Podgers et al. |
| 5,084,074 A | 1/1992 | Beer et al. |
| 5,122,264 A * | 6/1992 | Mohr ............... B67D 7/76 210/111 |
| 5,160,605 A | 11/1992 | Noestheden |
| 5,192,430 A * | 3/1993 | Mohr ............... B01D 36/001 210/453 |
| 5,332,900 A | 7/1994 | Witzke et al. |
| 5,376,215 A | 12/1994 | Ohta et al. |
| 5,409,025 A | 4/1995 | Semler et al. |
| 6,444,121 B1 * | 9/2002 | Maxwell ............ B01D 17/10 123/514 |
| 6,596,174 B1 * | 7/2003 | Marcus ............. B67D 7/766 210/764 |
| 6,763,856 B2 | 7/2004 | Healy |
| 6,907,899 B2 | 6/2005 | Yu et al. |
| 7,051,579 B2 | 5/2006 | Kenney et al. |
| 7,114,490 B2 | 10/2006 | Zdroik |
| 7,251,983 B2 | 8/2007 | Hutchinson |
| 7,726,336 B2 | 6/2010 | Dolson |
| 7,883,627 B1 | 2/2011 | Barrett |
| 8,141,577 B2 | 3/2012 | Wyper et al. |
| 8,282,023 B2 | 10/2012 | Olander et al. |
| 8,290,111 B1 | 10/2012 | Pop et al. |
| 8,511,351 B2 | 8/2013 | Watkins et al. |
| 8,539,829 B2 | 9/2013 | Bardsley et al. |
| 8,894,925 B2 | 11/2014 | Parfitt et al. |
| 9,194,856 B2 | 11/2015 | Liu et al. |
| 9,428,375 B2 * | 8/2016 | Sabo ................. B67D 7/3281 |
| 9,440,843 B2 | 9/2016 | Polzin |
| 9,530,290 B2 | 12/2016 | Hutchinson |
| 9,897,509 B2 | 2/2018 | Garrett |
| 10,226,736 B1 | 3/2019 | Cottingham |
| 10,238,759 B2 | 3/2019 | Smith |
| 10,239,745 B2 | 3/2019 | Cornett et al. |
| 10,865,098 B2 | 12/2020 | Gibson et al. |
| 11,111,130 B2 * | 9/2021 | Bevins ................. B67D 7/78 |
| 11,352,248 B2 * | 6/2022 | Schultz ............. B01D 36/005 |
| 11,365,113 B2 * | 6/2022 | Schultz ............... B67D 7/32 |
| 2005/0008532 A1 | 1/2005 | Jenkins et al. |
| 2005/0121374 A1 * | 6/2005 | Girondi ............. B01D 36/003 210/97 |
| 2006/0207430 A1 | 9/2006 | Huang et al. |
| 2007/0114160 A1 | 5/2007 | Giolitti et al. |
| 2009/0006026 A1 | 1/2009 | Clover |
| 2009/0045925 A1 | 2/2009 | Demin et al. |
| 2009/0114676 A1 | 5/2009 | Showers et al. |
| 2009/0173698 A1 | 7/2009 | Sundeng |
| 2010/0276424 A1 | 11/2010 | Ross |
| 2011/0259088 A1 | 10/2011 | Fisher et al. |
| 2012/0206253 A1 | 8/2012 | Taniguchi |
| 2013/0256161 A1 | 10/2013 | Crary et al. |
| 2013/0341333 A1 | 12/2013 | Herdman et al. |
| 2014/0053943 A1 | 2/2014 | Sabo et al. |
| 2016/0236927 A1 | 8/2016 | Perry |
| 2016/0331856 A1 | 11/2016 | Smith |
| 2017/0030521 A1 | 2/2017 | Markham et al. |
| 2018/0003615 A1 | 1/2018 | Kessler et al. |
| 2018/0257925 A1 | 9/2018 | Schultz et al. |
| 2020/0017351 A1 | 1/2020 | Schultz et al. |
| 2022/0289554 A1 | 9/2022 | Schultz et al. |

FOREIGN PATENT DOCUMENTS

| | | |
|---|---|---|
| EP | 0718216 A1 | 6/1996 |
| EP | 2567944 A1 | 3/2013 |
| FR | 2908760 A1 | 5/2008 |
| GB | 2129329 A | 5/1984 |
| JP | 2005-076070 A | 3/2005 |
| JP | 2008-155890 A | 7/2008 |
| JP | 2010-116842 A | 5/2010 |
| WO | 98/32693 A1 | 7/1998 |
| WO | 99/45272 A1 | 9/1999 |
| WO | 2008/059288 A1 | 5/2008 |
| WO | 2012/172286 A1 | 12/2012 |

OTHER PUBLICATIONS

Battelle Memorial Institute, "Corrosion in Systems Storing and Dispensing Ultra Low Sulfur Diesel (ULSD)," Hypotheses Investigation, Sep. 5, 2012.

Clean Diesel Fuel Alliance, "Guidance for Underground Storage Tank Management at ULSD Dispensing Facilities," available at least as early as May 23, 2017, 10 pages.

Ed Fowler, et al., "Ethanol Related Corrosion in Submersible Turbine Pump Sumps (STPs)", presentation dated Mar. 2011, presentation available online at http://www.astswmo.org/Files/Meetings/2011/2011-UST-CP-Workshop/FOWLER-STPcorrosionEPA3.SGPP.pdf, at least as early as Feb. 23, 2012.

International Preliminary Report on Patentability received for PCT Patent Application No. PCT/US2018/021350, dated Sep. 19, 2019, 15 pages.

International Preliminary Report on Patentability received for PCT Patent Application No. PCT/US2019/049104, dated Sep. 16, 2021, 11 pages.

International Search Report and Written Opinion received for PCT Patent Application No. PCT/US2018/021350, dated Oct. 11, 2018, 19 pages.

International Search Report and Written Opinion received for PCT Patent Application No. PCT/US2019/049104, dated Dec. 10, 2019, 13 pages.

(56) References Cited

OTHER PUBLICATIONS

John T. Wilson, et al., "Relationship Between Ethanol in Fuel and Corrosion in STP Sumps", available at least early as Apr. 3, 2012.
M. Lorenzini et al., "Ultraviolet Light (UV-C) Irradiation as an Alternative Technology for the Control of Microoorangisms in Grape Juice and Wine," 2019, 8 pages.
PEI Journal, "The Big E", 2nd Quarter, 2011.
Steel Tank Institute, "Steel Tank Institute Recommended Practice for Storage Tank Maintenance," R111 Revision, 2nd Edition, Mar. 2016, 21 pages.
U.S. Environmental Protection Agency, "ETVoice", Jan./Feb. 2012.
U.S. Environmental Protection Agency, "Investigation of Corrosion-Influencing Factors in Underground Storage Tanks With Diesel Service," EPA 510-R-16-001, Jul. 2016, 68 pages.
U.S. Environmental Protection Agency, "UST Systems: Inspecting and Maintaining Sumps and Spill Buckets", available online at http:www.epa/gov/ousl/pubs/sumps/%20manual%204-28-05.pdf,at least as early as Jul. 2012.
Uptime Institute, "Reconsider Your Diesel Fuel SUpply," printed Jun. 7, 2017, 11 pages.

\* cited by examiner

| No. | Control | 23 hours | 80 hours | 130 hours |
|---|---|---|---|---|
| 1 | | | | |
| 2 | | | | |
| 3 | | | | |
| 4 | | | | |
| 5 | | | | |

FIG. 7

METHOD AND APPARATUS FOR LIMITING ACIDIC CORROSION AND CONTAMINATION IN FUEL DELIVERY SYSTEMS

CROSS REFERENCE TO RELATED APPLICATIONS

This application is a division of U.S. patent application Ser. No. 15/914,535, filed Mar. 7, 2018, which claims priority to U.S. Provisional Patent Application Ser. No. 62/468,033 filed Mar. 7, 2017, U.S. Provisional Patent Application Ser. No. 62/509,506 filed May 22, 2017, U.S. Provisional Patent Application Ser. No. 62/520,891 filed Jun. 16, 2017, and U.S. Provisional Patent Application Ser. No. 62/563,596 filed Sep. 26, 2017, the disclosures of which are hereby expressly incorporated by reference herein in their entireties.

FIELD OF THE DISCLOSURE

The present disclosure relates to controlling fuel delivery systems and, in particular, to a method and apparatus for controlling fuel delivery systems to limit acidic corrosion, and/or to limit the accumulation of water and particulate matter in stored fuel.

BACKGROUND OF THE DISCLOSURE

A fuel delivery system typically includes one or more underground storage tanks that store various fuel products and one or more fuel dispensers that dispense the fuel products to consumers. The underground storage tanks may be coupled to the fuel dispensers via corresponding underground fuel delivery lines.

In the context of an automobile fuel delivery system, for example, the fuel products may be delivered to consumers' automobiles. In such systems, the fuel products may contain a blend of gasoline and alcohol, specifically ethanol. Blends having about 2.5 vol. % ethanol ("E-2.5"), 5 vol. % ethanol ("E-5"), 10 vol. % ethanol ("E-10"), or more, in some cases up to 85 vol. % ethanol ("E-85"), are now available as fuel for cars and trucks in the United States and abroad. Other fuel products include diesel and biodiesel, for example.

Sumps (i.e., pits) may be provided around the equipment of the fuel delivery system. Such sumps may trap liquids and vapors to prevent environmental releases. Also, such sumps may facilitate access and repairs to the equipment. Sumps may be provided in various locations throughout the fuel delivery system. For example, dispenser sumps may be located beneath the fuel dispensers to provide access to piping, connectors, valves, and other equipment located beneath the fuel dispensers. As another example, turbine sumps may be located above the underground storage tanks to provide access to turbine pump heads, piping, leak detectors, electrical wiring, and other equipment located above the underground storage tanks.

Underground storage tanks and sumps may experience premature corrosion. Efforts have been made to control such corrosion with fuel additives, such as biocides and corrosion inhibitors. However, the fuel additives may be ineffective against certain microbial species, become depleted over time, and cause fouling, for example. Efforts have also been made to control such corrosion with rigorous and time-consuming water maintenance practices, which are typically disfavored by retail fueling station operators.

Water and/or particulate matter sometimes also contaminates the fuel stored in underground storage tanks. Because these contaminants are generally heavier than the fuel product itself, any water or particulate matter found in the storage tank is generally confined to a "layer" of fuel mixed with contaminants at bottom of the tank. Because dispensation of these contaminants may have adverse effects on vehicles or other end-use applications, efforts have been made to timely detect and remediate such contaminants.

SUMMARY

The present disclosure relates to a method and apparatus for controlling a fuel delivery system to limit acidic corrosion. An exemplary control system includes a controller, at least one monitor, an output, and a remediation system. The monitor of the control system may collect and analyze data indicative of a corrosive environment in the fuel delivery system. The output of the control system may automatically warn an operator of the fueling station of the corrosive environment so that the operator can take preventative or corrective action. The remediation system of the control system may take at least one corrective action to remediate the corrosive environment in the fuel delivery system.

The present disclosure further relates to a method and apparatus for filtration of fuel contained in a storage tank, in which activation of a fuel dispensation pump concurrently activates a filtration system. In particular, a portion of pressurized fuel delivered by the dispensation pump is diverted to an eductor designed to create a vacuum by the venturi effect. This vacuum draws fluid from the bottom of the storage tank, at a point lower than the intake for the dispensation pump so that any water or particulate matter at the bottom of the storage tank is delivered to the eductor before it can reach the dispensation pump intake. The eductor delivers a mix of the diverted fuel and the tank-bottom fluid to a filter, where any entrained particulate matter or water is filtered out and removed from the product stream. Clean, filtered fuel is then delivered back to the storage tank.

According to an embodiment of the present disclosure, a fuel delivery system is provided including a storage tank containing a fuel product, a fuel delivery line in communication with the storage tank, at least one monitor that collects data indicative of a corrosive environment in the fuel delivery system, a controller in communication with the at least one monitor to receive collected data from the at least one monitor, and a remediation system configured to take at least one corrective action to remediate the corrosive environment when activated by the controller.

According to another embodiment of the present disclosure, a fuel delivery system is provided including a storage tank containing a fuel product, a fuel delivery line in communication with the storage tank, a monitor including a light source, a corrosive target material exposed to a corrosive environment in the fuel delivery system, and a detector configured to detect light from the light source through the target material, and a controller in communication with the monitor.

According to yet another embodiment of the present disclosure, a fuel delivery system is provided including a storage tank containing a fuel product, a sump, a pump having a first portion positioned in the sump and a second portion positioned in the storage tank, and a water filtration system. The water filtration system includes a water filter positioned in the sump and configured to separate the fuel product into a filtered fuel product and a separated water product, a fuel inlet passageway in fluid communication with the storage tank and the water filter via the pump to direct the fuel product to the water filter, a fuel return passageway in fluid communication with the water filter and the storage tank to return the filtered fuel product to the storage tank, and a water removal passageway in fluid communication with the water filter to drain the separated water product from the water filter.

According to still another embodiment of the present disclosure, a fuel delivery system is provided including a water filtration system. The water filtration system includes a filter configured to separate a fuel product into a filtered fuel product and a separated water product, an eductor configured to receive a flow of fuel from a fuel delivery pump and send the flow of fuel to the filter, and a vacuum port on the eductor configured to be operably connected to a source of contaminated fuel, such that the vacuum port draws the contaminated fuel into the flow of fuel through the eductor and delivers a mixture of fuel and contaminated fuel to the filter.

According to still another embodiment of the present disclosure, a fuel delivery system is disclosed including a storage tank containing a fuel product, a dispenser, a water filter, a fuel uptake line in fluid communication with the storage tank and the dispenser to deliver the fuel product to the dispenser, a filtration uptake line in fluid communication with the storage tank and the water filter to deliver the fuel product to the water filter, the water filter being configured to separate the fuel product into a filtered fuel product and a separated water product, a fuel return passageway in fluid communication with the water filter and the storage tank to return the filtered fuel product to the storage tank, and a water removal passageway in fluid communication with the water filter to drain the separated water product from the water filter.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein:

FIG. 7 includes photographs of the corrosive samples tested in Example 1;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
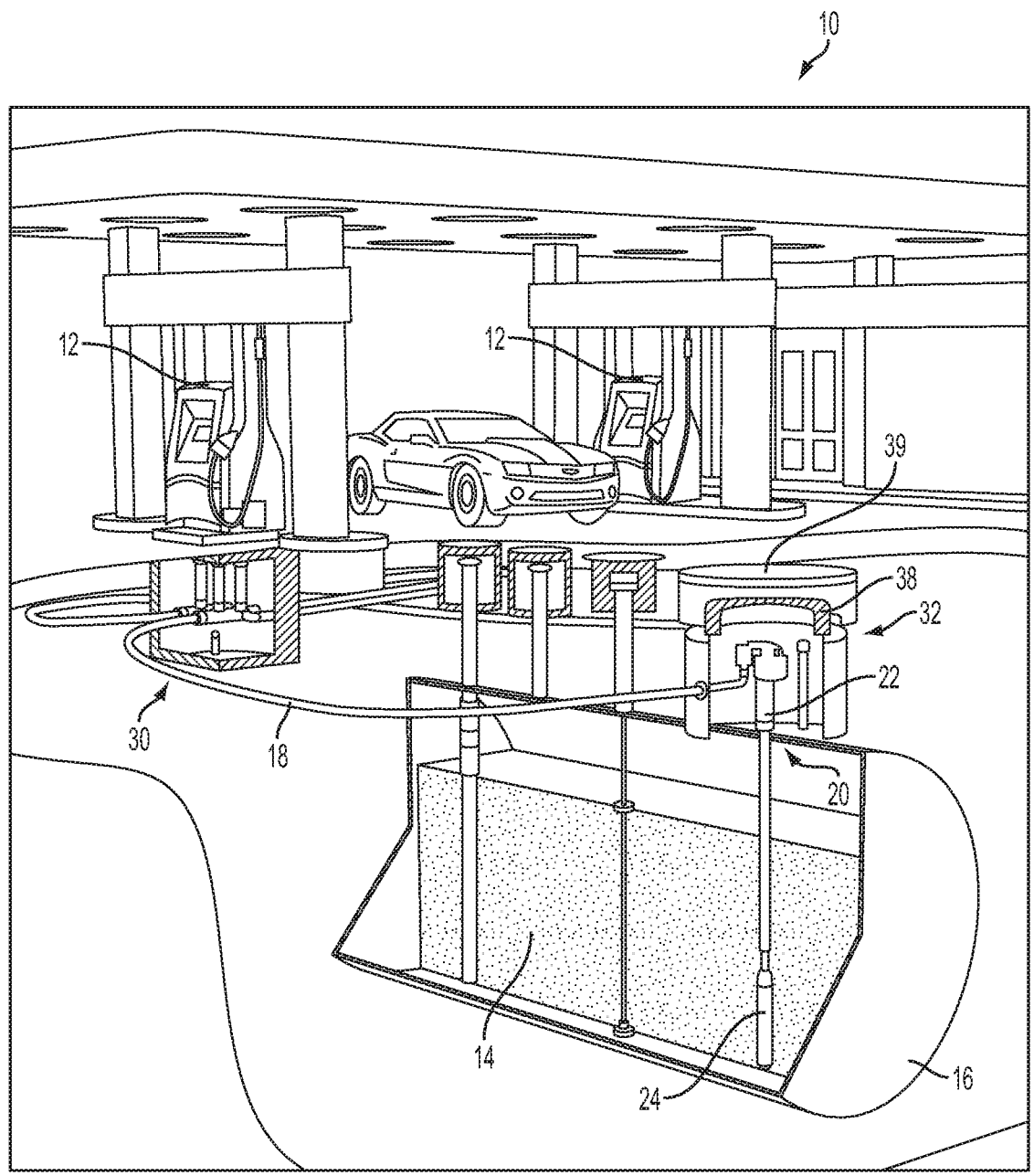
FIG. 1 depicts an exemplary fuel delivery system of the present disclosure showing above ground components, such as a fuel dispenser, and below ground components, such as a storage tank containing a fuel product, a fuel delivery line, a turbine sump, and a dispenser sump.

An exemplary fuel delivery system 10 is shown in FIG. 1. Fuel delivery system 10 includes a fuel dispenser 12 for dispensing a liquid fuel product 14 from a liquid storage tank 16 to consumers. Each storage tank 16 is fluidly coupled to one or more dispensers 12 via a corresponding fuel delivery line 18. Storage tank 16 and delivery line 18 are illustratively positioned underground, but it is also within the scope of the present disclosure that storage tank 16 and/or delivery line 18 may be positioned above ground.

Fuel delivery system 10 of FIG. 1 also includes a pump 20 to draw fuel product 14 from storage tank 16 and to convey fuel product 14 through delivery line 18 to dispenser 12. Pump 20 is illustratively a submersible turbine pump ("STP") having a turbine pump head 22 located above storage tank 16 and a submersible motor 24 located inside storage tank 16. However, it is within the scope of the present disclosure that other types of pumps may be used to transport fuel product 14 through fuel delivery system 10.

Figure 2:
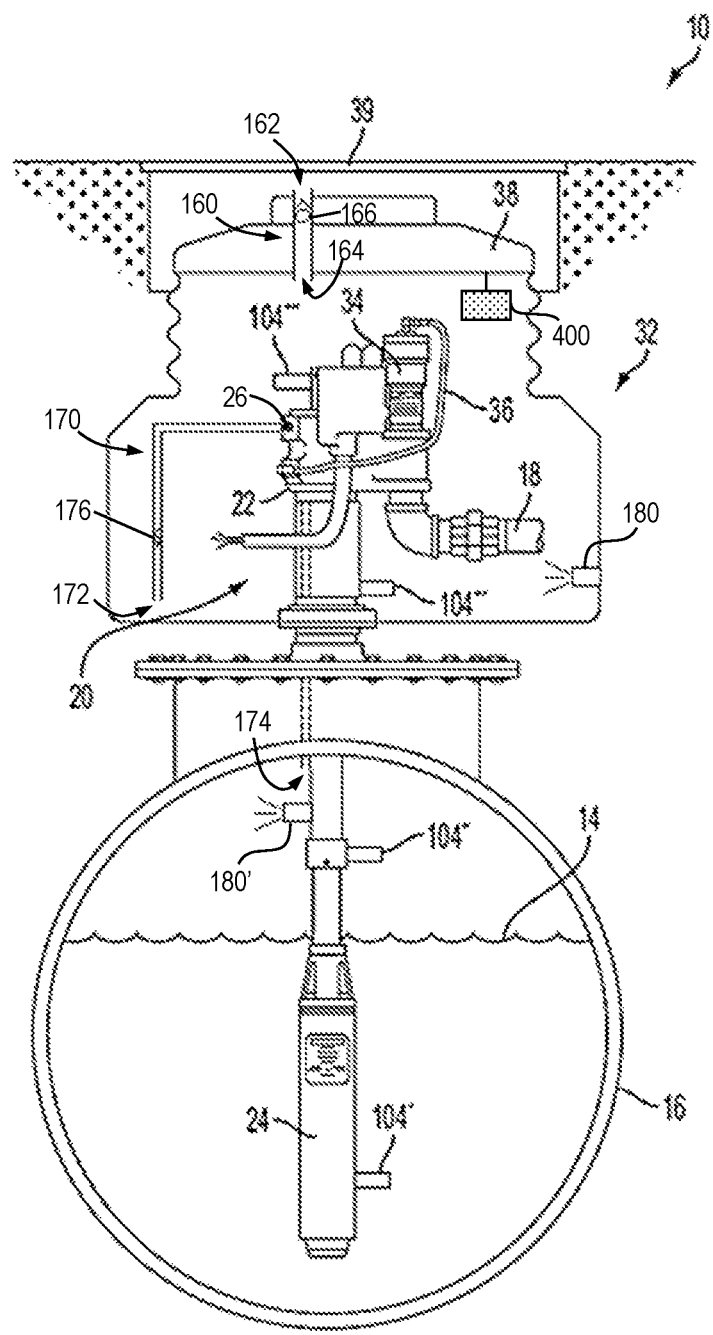
FIG. 2 is a cross-sectional view of the storage tank and the turbine sump of FIG. 1.

Fuel delivery system 10 of FIG. 1 further includes various underground sumps (i.e., pits). A first, dispenser sump 30 is provided beneath dispenser 12 to protect and provide access to piping (e.g., delivery line 18), connectors, valves, and other equipment located therein, and to contain any materials that may be released beneath dispenser 12. A second, turbine sump 32, which is also shown in FIG. 2, is provided above storage tank 16 to protect and provide access to pump 20, piping (e.g., delivery line 18), leak detector 34, electrical wiring 36, and other equipment located therein. Turbine sump 32 is illustratively capped with an underground lid 38 and a ground-level manhole cover 39, which protect the equipment inside turbine sump 32 when installed and allow access to the equipment inside turbine sump 32 when removed.

According to an exemplary embodiment of the present disclosure, fuel delivery system 10 is an automobile fuel delivery system. In this embodiment, fuel product 14 may be a gasoline/ethanol blend that is delivered to consumers' automobiles, for example. The concentration of ethanol in the gasoline/ethanol blended fuel product 14 may vary from 0 vol. % to 15 vol. % or more. For example, fuel product 14 may contain about 2.5 vol. % ethanol ("E-2.5"), about 5 vol. % ethanol ("E-5"), about 7.5 vol. % ethanol ("E-7.5"), about 10 vol. % ethanol ("E-10"), about 15 vol. % ethanol ("E-15"), or more, in some cases up to about 85 vol. % ethanol ("E-85"). As discussed in U.S. Publication No. 2012/0261437, the disclosure of which is expressly incorporated herein by reference in its entirety, the ethanol may attract water into the gasoline/ethanol blended fuel product 14. The water in fuel product 14 may be present in a dissolved state, an emulsified state, or a free water state. Eventually, the water may also cause phase separation of fuel product 14.

In addition to being present in storage tank 16 as part of the gasoline/ethanol blended fuel product 14, ethanol may find its way into other locations of fuel delivery system 10 in a vapor or liquid state, including dispenser sump 30 and turbine sump 32. In the event of a fluid leak from dispenser 12, for example, some of the gasoline/ethanol blended fuel product 14 may drip from dispenser 12 into dispenser sump 30 in a liquid state. Also, in the event of a vapor leak from storage tank 16, vapor in the ullage of storage tank 16 may escape from storage tank 16 and travel into turbine sump 32. In certain situations, turbine sump 32 and/or components contained therein (e.g., metal fittings, metal valves, metal plates) may be sufficiently cool in temperature to condense the ethanol vapor back into a liquid state in turbine sump 32. Along with ethanol, water from the surrounding soil, fuel product 14, or another source may also find its way into sumps 30, 32 in a vapor or liquid state, such as by dripping into sumps 30, 32 in a liquid state or by evaporating and then condensing in sumps 30, 32. Ethanol and/or water leaks into sumps 30, 32 may occur through various connection points in sumps 30, 32, for example. Ethanol and/or water may escape from ventilated sumps 30, 32 but may become trapped in unventilated sumps 30, 32.

In the presence of certain bacteria and water, ethanol that is present in fuel delivery system 10 may be oxidized to produce acetate, according to Reaction I below.

$$CH_3CH_2OH+H_2O \rightarrow CH_3COO^-+H^++2H_2 \qquad (I)$$

The acetate may then be protonated to produce acetic acid, according to Reaction II below.

$$CH_3COO^-+H^+ \rightarrow CH_3COOH \qquad (II)$$

The conversion of ethanol to acetic acid may also occur in the presence of oxygen according to Reaction III below.

$$2CH_3CH_2OH+O_2 \rightarrow 2CH_3COOH+2H_2O \qquad (III)$$

Acetic acid producing bacteria or AAB may produce acetate and acetic acid by a metabolic fermentation process, which is used commercially to produce vinegar, for example. Acetic acid producing bacteria generally belong to the Acetobacteraceae family, which includes the genera *Acetobacter*, *Gluconobacter*, and *Gluconacetobacter*. Acetic acid producing bacteria are very prevalent in nature and may be present in the soil around fuel delivery system 10, for example. Such bacteria may find their way into sumps 30, 32 to drive Reactions I-III above, such as when soil or debris falls into sumps 30, 32 or when rainwater seeps into sumps 30, 32.

The products of Reactions I-III above may reach equilibrium in sumps 30, 32, with some of the acetate and acetic acid dissolving into liquid water that is present in sumps 30, 32, and some of the acetate and acetic acid volatilizing into a vapor state. In general, the amount acetate or acetic acid that is present in the vapor state is proportional to the amount of acetate or acetic acid that is present in the liquid state (i.e, the more acetate or acetic acid that is present in the vapor state, the more acetate or acetic acid that is present in the liquid state).

Even though acetic acid is classified as a weak acid, it may be corrosive to fuel delivery system 10, especially at high concentrations. For example, the acetic acid may react to deposit metal oxides (e.g., rust) or metal acetates on metallic fittings of fuel delivery system 10. Because Reactions I-III are microbiologically-influenced reactions, these deposits in fuel delivery system 10 may be tubular or globular in shape.

Figure 3:
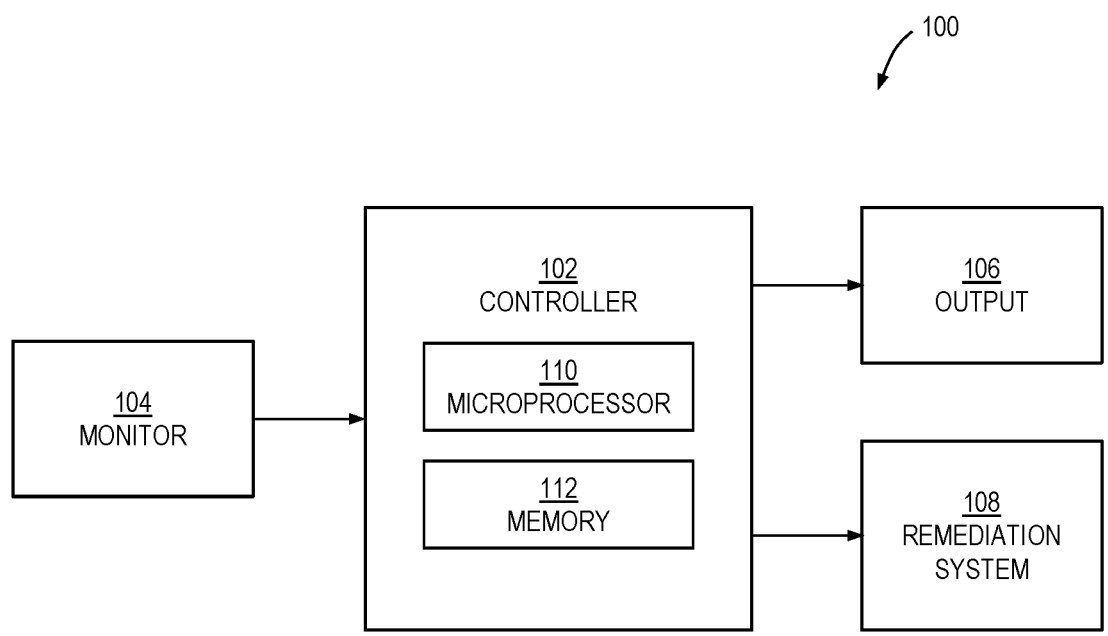
FIG. 3 is a schematic view of an exemplary control system of the present disclosure, the control system including a controller, at least one monitor, an output, and a remediation system.

To limit corrosion in fuel delivery system 10, a control system 100 and a corresponding monitoring method are provided herein. As shown in FIG. 3, the illustrative control system 100 includes controller 102, one or more monitors 104 in communication with controller 102, output 106 in communication with controller 102, and remediation system 108 in communication with controller 102, each of which is described further below.

Controller 102 of control system 100 illustratively includes a microprocessor 110 (e.g., a central processing unit (CPU)) and an associated memory 112. Controller 102 may be any type of computing device capable of accessing a computer-readable medium having one or more sets of instructions (e.g., software code) stored therein and executing the instructions to perform one or more of the sequences, methodologies, procedures, or functions described herein. In general, controller 102 may access and execute the instructions to collect, sort, and/or analyze data from monitor 104, determine an appropriate response, and communicate the response to output 106 and/or remediation system 108. Controller 102 is not limited to being a single computing device, but rather may be a collection of computing devices (e.g., a collection of computing devices accessible over a network) which together execute the instructions. The instructions and a suitable operating system for executing the instructions may reside within memory 112 of controller 102, for example. Memory 112 may also be configured to store real-time and historical data and measurements from monitors 104, as well as reference data. Memory 112 may store information in database arrangements, such as arrays and look-up tables.

Controller 102 of control system 100 may be part of a larger controller that controls the rest of fuel delivery system 10. In this embodiment, controller 102 may be capable of operating and communicating with other components of fuel delivery system 10, such as dispenser 12 (FIG. 1), pump 20 (FIG. 2), and leak detector 34 (FIG. 2), for example. An exemplary controller 102 is the TS-550 Evo® Fuel Management System available from Franklin Fueling Systems Inc. of Madison, Wis.

Monitor 104 of control system 100 is configured to automatically and routinely collect data indicative of a corrosive environment in fuel delivery system 10. In operation, monitor 104 may draw in a liquid or vapor sample from fuel delivery system 10 and directly test the sample or test a target material that has been exposed to the sample, for example. In certain embodiments, monitor 104 operates continuously, collecting samples and measuring data approximately once every second or minute, for example. Monitor 104 is also configured to communicate the collected data to controller 102. In certain embodiments, monitor 104 manipulates the data before sending the data to controller 102. In other embodiments, monitor 104 sends the data to controller 102 in raw form for manipulation by controller 102. The illustrative monitor 104 is wired to controller 102, but it is also within the scope of the present disclosure that monitor 104 may communicate wirelessly (e.g., via an internet network) with controller 102.

Depending on the type of data being collected by each monitor 104, the location of each monitor 104 in fuel delivery system 10 may vary. Returning to the illustrated embodiment of FIG. 2, for example, monitor 104' is positioned in the liquid space (e.g, middle or bottom) of storage tank 16 to collect data regarding the liquid fuel product 14 in storage tank 16, monitor 104" is positioned in the ullage or vapor space (i.e., top) of storage tank 16 to collect data regarding any vapors present in storage tank 16, monitor 104''' is positioned in the liquid space (i.e., bottom) of turbine sump 32 to collect data regarding any liquids present in turbine sump 32, and monitor 104'''' is positioned in the vapor space (i.e., top) of turbine sump 32 to collect data regarding any vapors present in turbine sump 32. Monitor 104 may be positioned in other suitable locations of fuel delivery system 10, including delivery line 18 and dispenser sump 30 (FIG. 1), for example. Various monitors 104 for use in control system 100 of FIG. 3 are discussed further below.

Output 106 of control system 100 may be capable of communicating an alarm or warning from controller 102 to an operator. Output 106 may include a visual indication device (e.g., a gauge, a display screen, lights, a printer), an audio indication device (e.g., a speaker, an audible alarm), a tactile indication device, or another suitable device for communicating information to the operator, as well as combinations thereof. Controller 102 may transmit information to output 106 in real-time, or controller 102 may store information in memory 112 for subsequent transmission or download to output 106.

Remediation system 108 of control system 100 may be capable of taking at least one corrective action to remediate the corrosive environment in fuel delivery system 10. Various embodiments of remediation system 108 are described below.

The illustrative output 106 and remediation system 108 are wired to controller 102, but it is also within the scope of the present disclosure that output 106 and/or remediation system 108 may communicate wirelessly (e.g., via an internet network) with controller 102. For example, to facilitate communication between output 106 and the operator, output 106 may be located in the operator's control room or office.

In operation, and as discussed above, controller 102 collects, sorts, and/or analyzes data from monitor 104, determines an appropriate response, and communicates the response to output 106 and/or remediation system 108. According to an exemplary embodiment of the present disclosure, output 106 warns the operator of a corrosive environment in fuel delivery system 10 and/or remediation system 108 takes corrective action before the occurrence of any corrosion or any significant corrosion in fuel delivery system 10. In this embodiment, corrosion may be prevented or minimized. It is also within the scope of the present disclosure that output 106 may alert the operator to the occurrence of corrosion in fuel delivery system 10 and/or remediation system 108 may take corrective action to at least avoid further corrosion.

Various factors may influence whether controller 102 issues an alarm or warning from output 106 that a corrosive environment is present in fuel delivery system 10 or becoming more likely to develop. Similar factors may also influence whether controller 102 instructs remediation system 108 to take corrective action in response to the corrosive environment. As discussed further below, these factors may be evaluated based on data obtained from one or more monitors 104.

One factor indicative of a corrosive environment includes the concentration of acidic molecules in fuel delivery system 10, with controller 102 issuing an alarm or warning from output 106 and/or activating remediation system 108 when the measured concentration of acidic molecules in fuel delivery system 10 exceeds an acceptable concentration of acidic molecules in fuel delivery system 10. The concentration may be expressed in various units. For example, controller 102 may activate output 106 and/or remediation system 108 when the measured concentration of acidic molecules in fuel delivery system 10 exceeds 25 ppm, 50 ppm, 100 ppm, 150 ppm, 200 ppm, or more, or when the measured concentration of acidic molecules in fuel delivery system 10 exceeds 25 mg/L, 50 mg/L, 100 mg/L, 150 mg/L, 200 mg/L, or more. At or beneath the acceptable concentration, corrosion in fuel delivery system 10 may be limited. Controller 102 may also issue an alarm or warning from output 106 and/or activate remediation system 108 when the concentration of acidic molecules increases at an undesirably high rate.

Another factor indicative of a corrosive environment includes the concentration of hydrogen ions in fuel delivery system 10, with controller 102 issuing an alarm or warning from output 106 and/or activating remediation system 108 when the measured concentration of hydrogen ions in fuel delivery system 10 exceeds an acceptable concentration of hydrogen ions in fuel delivery system 10. For example, controller 102 may activate output 106 and/or remediation system 108 when the hydrogen ion concentration causes the pH in fuel delivery system 10 to drop below 5, 4, 3, or 2, for example. Within the acceptable pH range, corrosion in fuel delivery system 10 may be limited. Controller 102 may also issue an alarm or warning from output 106 and/or activate remediation system 108 when the concentration of hydrogen ions increases at an undesirably high rate.

Yet another factor indicative of a corrosive environment includes the concentration of bacteria in fuel delivery system 10, with controller 102 issuing an alarm or warning from output 106 and/or activating remediation system 108 when the measured concentration of bacteria in fuel delivery system 10 exceeds an acceptable concentration of bacteria in fuel delivery system 10. At or beneath the acceptable concentration, the production of corrosive materials in fuel delivery system 10 may be limited. Controller 102 may also issue an alarm or warning from output 106 and/or activate remediation system 108 when the concentration of bacteria increases at an undesirably high rate.

Yet another factor indicative of a corrosive environment includes the concentration of water in fuel delivery system 10, with controller 102 issuing an alarm or warning from output 106 and/or activating remediation system 108 when the measured concentration of water in fuel delivery system 10 exceeds an acceptable concentration of water in fuel delivery system 10. At or beneath the acceptable concentration, the production of corrosive materials in fuel delivery system 10 may be limited. Controller 102 may also issue an alarm or warning from output 106 and/or activate remediation system 108 when the concentration of water increases at an undesirably high rate. The water may be present in liquid and/or vapor form.

Controller 102 may be programmed to progressively vary the alarm or warning communication from output 106 as the risk of corrosion in fuel delivery system 10 increases. For example, controller 102 may automatically trigger: a minor alarm (e.g., a blinking light) when monitor 104 detects a relatively low acid concentration level (e.g., 5 ppm) in fuel delivery system 10 or a relatively steady acid concentration level over time; a moderate alarm (e.g., an audible alarm) when monitor 104 detects a moderate acid concentration level (e.g., 10 ppm) in fuel delivery system 10 or a moderate increase in the acid concentration level over time; and a severe alarm (e.g., a telephone call or an e-mail to the gas station operator) when monitor 104 detects a relatively high acid concentration level (e.g., 25 ppm) in fuel delivery system 10 or a relatively high increase in the acid concentration level over time.

The alarm or warning communication from output 106 allows the operator to manually take precautionary or corrective measures to limit corrosion of fuel delivery system 10. For example, if an alarm or warning communication is signaled from turbine sump 32 (FIG. 2), the operator may remove manhole cover 39 and lid 38 to clean turbine sump 32, which may involve removing bacteria and potentially corrosive liquids and vapors from turbine sump 32. As another example, the operator may inspect fuel delivery system 10 for a liquid leak or a vapor leak that allowed ethanol and/or its acidic reaction products to enter turbine sump 32 in the first place.

Even if no immediate action is required, the alarm or warning communication from output 106 may allow the operator to better plan for and predict when such action may become necessary. For example, the minor alarm from output 106 may indicate that service should be performed within about 2 months, the moderate alarm from output 106 may indicate that service should be performed within about 1 month, and the severe alarm from output 106 may indicate that service should be performed within about 1 week.

As discussed above, control system 100 includes one or more monitors 104 that collect data indicative of a corrosive environment in fuel delivery system 10. Each monitor 104 may vary in the type of data that is collected, the type of sample that is evaluated for testing, and the location of the sample that is evaluated for testing, as exemplified below.

Figure 4:
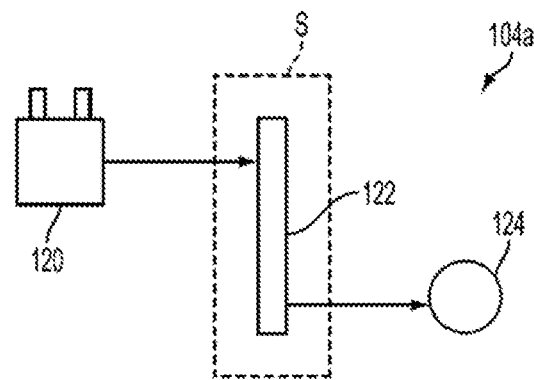
FIG. 4 is a schematic view of a first exemplary electrical monitor for use in the control system of FIG. 3.

In one embodiment, monitor 104 collects electrical data indicative of a corrosive environment in fuel delivery system 10. An exemplary electrical monitor 104a is shown in FIG. 4 and includes an energy source 120, a corrosive target material 122 that is exposed to a liquid or vapor sample S from fuel delivery system 10, and a sensor 124. To enhance the longevity of monitor 104a, energy source 120 and/or sensor 124 may be protected from any corrosive environment in fuel delivery system 10, unlike target material 122. Target material 122 may be designed to corrode before the equipment of fuel delivery system 10 corrodes. Target material 122 may be constructed of or coated with a material that is susceptible to acidic corrosion, such as copper or low carbon steel. Also, target material 122 may be relatively thin or small in size compared to the equipment of fuel delivery system 10 such that even a small amount of corrosion will impact the structural integrity of target material 122. For example, target material 122 may be in the form of a thin film or wire.

In use, energy source 120 directs an electrical current through target material 122. When target material 122 is intact, sensor 124 senses the electrical current traveling through target material 122. However, when exposure to sample S causes target material 122 to corrode and potentially break, sensor 124 will sense a decreased electrical current, or no current, traveling through target material 122. It is also within the scope of the present disclosure that the corrosion and/or breakage of target material 122 may be detected visually, such as by using a camera as sensor 124. First monitor 104a may share the data collected by sensor 124 with controller 102 (FIG. 3) to signal a corrosive environment in fuel delivery system 10 when the electrical current reaches an undesirable level or changes at an undesirable rate, for example. After use, the corroded target material 122 may be discarded and replaced.

Figure 5:
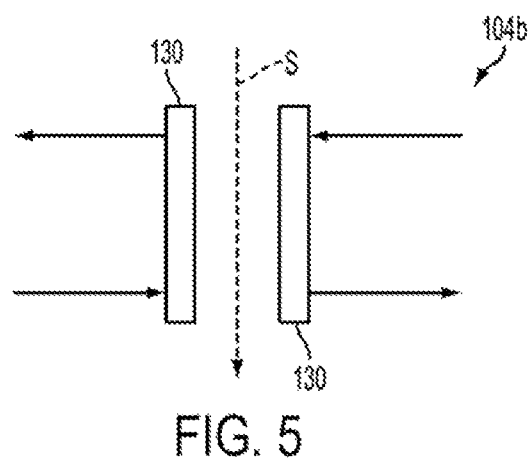
FIG. 5 is a schematic view of a second exemplary electrical monitor for use in the control system of FIG. 3.

Another exemplary electrical monitor 104b is shown in FIG. 5 and includes opposing, charged metal plates 130. The electrical monitor 104b operates by measuring electrical properties (e.g., capacitance, impedance) of a liquid or vapor sample S that has been withdrawn from fuel delivery system 10. In the case of a capacitance monitor 104b, for example, the sample S is directed between plates 130. Knowing the size of plates 130 and the distance between plates 130, the dielectric constant of the sample S may be calculated. As the quantity of acetate, acetic acid, and/or water in the sample S varies, the dielectric constant of the sample S may also vary. The electrical monitor 104b may share the collected data with controller 102 (FIG. 3) to signal a corrosive environment in fuel delivery system 10 when the dielectric constant reaches an undesirable level or changes at an undesirable rate, for example. One example of electrical monitor 104b is a water content monitor that may be used to monitor the water content of fuel product 14 or another sample S from fuel delivery system 10. An exemplary water content monitor is the ICM-W monitor available from MP Filtri, which uses a capacitive sensor to measure the relative humidity (RH) of the tested fluid. As the RH increases toward a saturation point, the water in the fluid may transition from a dissolved state, to an emulsified state, to a free water state. Other exemplary water content monitors are described in the above-incorporated U.S. Publication No. 2012/0261437. Another example of electrical monitor 104b is a humidity sensor that may be used to monitor the humidity in the vapor space of storage tank 16 and/or turbine sump 32.

In another embodiment, monitor 104 collects elecrochemical data indicative of a corrosive environment in fuel delivery system 10. An exemplary electrochemical monitor (not shown) performs potentiometric titration of a sample that has been withdrawn from fuel delivery system 10. A suitable potentiometric titration device includes an electrochemical cell with an indicator electrode and a reference electrode that maintains a consistent electrical potential. As a titrant is added to the sample and the electrodes interact with the sample, the electric potential across the sample is measured. Potentiometric or chronopotentiometric sensors, which may be based on solid-state reversible oxide films, such as that of iridium, may be used to measure potential in the cell. As the concentration of acetate or acetic acid in the sample varies, the potential may also vary. The potentiometric titration device may share the collected data with controller 102 (FIG. 3) to signal a corrosive environment in fuel delivery system 10 when the potential reaches an undesirable level or changes at an undesirable rate, for example. An electrochemical monitor may also operate by exposing the sample to an electrode, performing a reductionoxidation with the sample at the electrode, and measuring the resulting current, for example.

Figure 6:
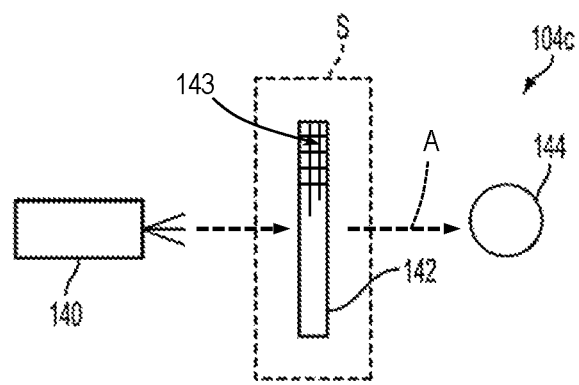
FIG. 6 is a schematic view of a third exemplary optical monitor for use in the control system of FIG. 3.

In yet another embodiment, monitor 104 collects optical data indicative of a corrosive environment in fuel delivery system 10. An exemplary optical monitor 104c is shown in FIG. 6 and includes a light source 140 (e.g., LED, laser), an optical target material 142 that is exposed to a liquid or vapor sample S from fuel delivery system 10, and an optical detector 144 (e.g., photosensor, camera). To enhance the safety of monitor 104c, light source 140 may be a low-energy and high-output device, such as a green LED. Target material 142 may be constructed of or coated with a material (e.g., an acid-sensitive polymer) that changes optical properties (e.g., color, transmitted light intensity) in the presence of the sample S.

Optical monitor 104c may enable real-time, continuous monitoring of fuel delivery system 10 by installing light source 140, target material 142, and detector 144 together in fuel delivery system 10. To enhance the longevity of this real-time monitor 104c, light source 140 and/or detector 144 may be protected from any corrosive environment in fuel delivery system 10, unlike target material 142. For example, light source 140 and/or detector 144 may be contained in a sealed housing, whereas target material 142 may be exposed to the surrounding environment in fuel delivery system 10.

Alternatively, optical monitor 104c may enable manual, periodic monitoring of fuel delivery system 10. During exposure, target material 142 may be installed alone in fuel delivery system 10. During testing, target material 142 may be periodically removed from fuel delivery system 10 and positioned between light source 140 and detector 144. In a first embodiment of the manual monitor 104c, light source 140 and detector 144 may be sold as a stand-alone, hand-held unit that is configured to receive the removed target material 142. In a second embodiment of the manual monitor 104c, light source 140 may be sold along with a software application to convert the operator's own smartphone or mobile device into a suitable detector 144. Detector 144 of monitor 104c may transmit information to controller 102 (FIG. 3) in real-time or store information in memory for subsequent transmission or download.

One suitable target material 142 includes a pH indicator that changes color when target material 142 is exposed to an acidic pH with $H^+$ protons, such as a pH less than about 5, 4, 3, or 2, for example. The optical properties of target material 142 may be configured to change before the equipment of fuel delivery system 10 corrodes. Detector 144 may use optical fibers as the sensing element (i.e., intrinsic sensors) or as a means of relaying signals to a remote sensing element (i.e., extrinsic sensors).

In use, light source 140 directs a beam of light toward target material 142. Before target material 142 changes color, for example, detector 144 may detect a certain reflection, transmission (i.e., spectrophotometry), absorption (i.e., densitometry), and/or refraction of the light beam from target material 142. However, after target material 142 changes color, detector 144 will detect a different reflection, transmission, absorption, and/or refraction of the light beam. It is also within the scope of the present disclosure that the changes in target material 142 may be detected visually, such as by using a camera (e.g., a smartphone camera) as detector 144. Third monitor 104c may share the data collected by detector 144 with controller 102 (FIG. 3) to signal a corrosive environment in fuel delivery system 10 when the color reaches an undesirable level or changes at an undesirable rate, for example.

Another suitable target material 142 includes a sacrificial, corrosive material that corrodes (e.g., rusts) when exposed to a corrosive environment in fuel delivery system 10. For example, the corrosive target material 142 may include copper or low carbon steel. The corrosive target material 142 may have a high surface area to volume ratio to provide detector 144 with a large and reliable sample size. For example, as shown in FIG. 6, the corrosive target material 142 may be in the form of a woven mesh or perforated sheet having a large plurality of pores 143.

In use, light source 140 directs a beam of light along an axis A toward the corrosive target material 142. Before target material 142 corrodes, detector 144 may detect a certain amount of light that passes from the light source 140 and through the open pores 143 of the illuminated target material 142 along the same axis A. However, as target material 142 corrodes, the material may visibly swell as rust accumulates in and around some or all of the pores 143. This accumulating rust may obstruct or prevent light from traveling through pores 143, so detector 144 (e.g., a photodiode) will detect a decreasing amount of light through the corroding target material 142. It is also within the scope of the present disclosure that the changes in target material 142 may be detected visually, such as by using a camera or another suitable imaging device as detector 144. Detector 144 may capture an image of the illuminated target material 142 and then evaluate the image (e.g., pixels of the image) for transmitted light intensity, specific light patterns, etc. As discussed above, third monitor 104c may share the data collected by detector 144 with controller 102 (FIG. 3) to signal a corrosive environment in fuel delivery system 10 when the transmitted light intensity reaches an undesirable level or changes at an undesirable rate, for example. After use, the corroded target material 142 may be discarded and replaced.

Another exemplary optical monitor 104c' is shown in FIGS. 16-19. Optical monitor 104c' of FIGS. 16-19 is similar to optical monitor 104c of FIG. 6 and includes several components and features in common with optical monitor 104c as indicated by the use of common reference numbers between optical monitors 104c, 104c', including a light source 140', a corrosive target material 142', and an optical detector 144'. Optical monitor 104c' may be mounted in the vapor space of storage tank 16 and/or turbine sump 32 of fuel delivery system 10 (FIG. 2).

The illustrative optical monitor 104c' is generally cylindrical in shape and has a longitudinal axis L. In the illustrated embodiment of FIG. 19, light source 140' and target material 142' are located on a first side of axis L (illustratively the right side of axis L), and optical detector 144' is located on a second side of axis L (illustratively the left side of axis L). Light source 140' and optical detector 144' are substantially coplanar and are located above target material 142'. The illustrative target material 142' is a L-shaped mesh sheet, with a vertical portion 145a' of target material 142' extending parallel to axis L and a horizontal portion 145b' of target material 142' extending perpendicular to axis L.

Figure 19:
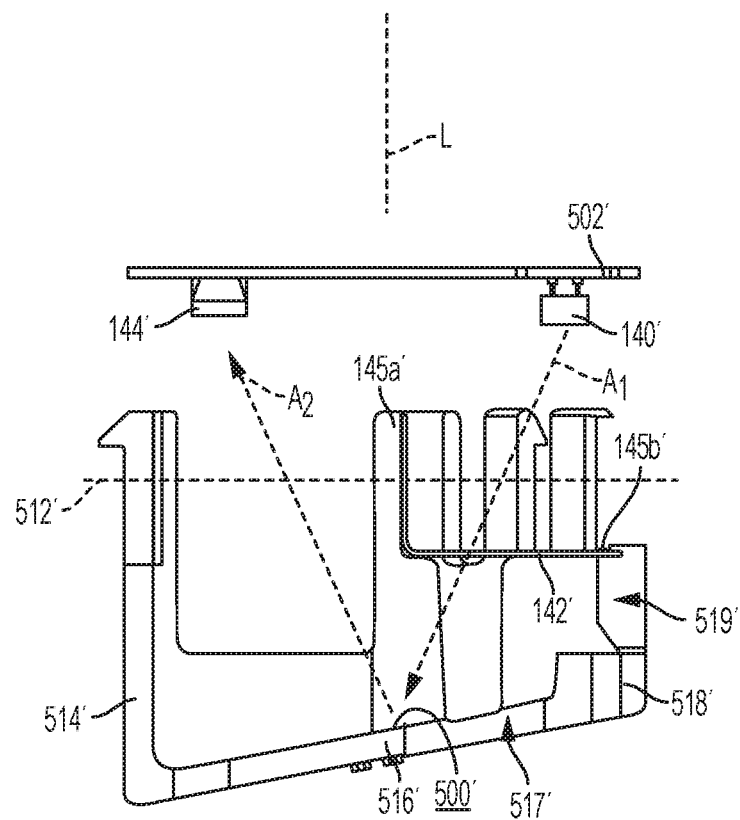
FIG. 19 is a partial cross-sectional view of the optical monitor of FIG. 16.

The illustrative optical monitor 104c' includes a reflective surface 500' positioned downstream of light source 140' and upstream of optical detector 144', wherein the reflective surface 500' is configured to reflect incident light from light source 140' toward optical detector 144'. In the illustrated embodiment of FIG. 19, the incident light from light source 140' travels downward and inward toward axis L along a first axis $A_1$ toward reflective surface 500', and then the reflected light from reflective surface 500' travels upward and outward from axis L along a second axis $A_2$ toward optical detector 144'. Reflective surface 500' may produce a specular reflection with the reflected light traveling along a single axis $A_2$, as shown in FIG. 19, or a diffuse reflection with the reflected light traveling in many different directions. Reflective surface 500' may be a shiny, mirrored, or otherwise reflective surface. Reflective surface 500' may be shaped and oriented to direct the reflected light toward optical detector 144'. For example, in FIG. 19, the reflective surface 500' is flat and is angled about 10 degrees relative to a horizontal plane to direct the reflected light toward optical detector 144'. The angled reflective surface 500' of FIG. 19 may also encourage drainage of any condensation (fuel or aqueous) that forms upon reflective surface 500'.

The illustrative optical monitor 104c' also includes at least one printed circuit board (PCB) 502' that mechanically and electrically supports light source 140' and optical detector 144'. PCB 502' may also allow light source 140' and/or optical detector 144' to communicate with controller 102 (FIG. 3). Light source 140' and optical detector 144' are illustratively coupled to the same PCB 502', but it is also within the scope of the present disclosure to use distinct PCBs.

The illustrative optical monitor 104c' further includes a cover 510', an upper housing 512', and a lower housing 514'. Lower housing 514' may be removably coupled to upper housing 512', such as using a snap connection 515', a threaded connection, or another removable connection.

Upper housing 512' contains light source 140', optical detector 144', and circuit board 502'. Upper housing 512' may be hermetically sealed to separate and protect its contents from the potentially corrosive environment in fuel delivery system 10 (FIG. 2). However, upper housing 512' may be at least partially or entirely transparent to permit the passage of light, as discussed further below.

Lower housing 514' contains target material 142' and reflective surface 500'. Reflective surface 500' may be formed directly upon lower housing 514' (e.g., a reflective coating) or may be formed on a separate component (e.g., a reflective panel) that is coupled to lower housing 514'. In the illustrated embodiment of FIG. 19, reflective surface 500' is located on bottom wall 516' of lower housing 514'. Unlike the contents of upper housing 512', which are separated from the vapors in fuel delivery system 10, the contents of lower housing 514', particularly target material 142', are exposed to the vapors in fuel delivery system 10. The illustrative lower housing 514' has bottom wall 516' with a plurality of bottom openings 517' and a side wall 518' with a plurality of side openings 519' to encourage the vapors in fuel delivery system 10 to enter lower housing 514' and interact with target material 142'. Openings 517', 519' may vary in shape, size, and location. In general, lower housing 514' should be designed to be sufficiently solid to support and protect its contents while being sufficiently open to expose its contents to the vapors in fuel delivery system 10. For example, the bottom openings 517' may be concentrated beneath target material 142'. Also, the side openings 519' adjacent to target material 142' may be relatively small, whereas the side openings 519' opposite from target material 142' may be relatively large.

In use, and as shown in FIG. 19, light source 140' directs a beam of light along the first axis $A_1$, through the transparent upper housing 512', and toward target material 142'. The L-shaped configuration of target material 142' may block any direct light pathways between light source 140' and reflective surface 500' to ensure that all of the light from light source 140' encounters target material 142' before reaching reflective surface 500'. The light that is able to pass through the pores 143' of target material 142' continues to reflective surface 500', which then reflects the light along the second axis $A_2$, back through the transparent upper housing 512', and to optical detector 144'. Optical detector 144' may signal a corrosive environment in fuel delivery system 10 when the transmitted light intensity through the corroding target material 142' reaches an undesirable level or changes at an undesirable rate, for example. After use, lower housing 514' may be detached (e.g., unsnapped) from upper housing 512' to facilitate removal and replacement of the corroded target material 142' and/or reflective surface 500' without disturbing the contents of upper housing 512'.

Optical monitor 104c' may be configured to detect one or more errors. If the light intensity detected by detector 144' is too high (e.g., at or near 100%), optical monitor 104c' may issue a "Target Material Error" to inform the operator that target material 142' may be missing or damaged. To avoid false alarms caused by exposure to ambient light, such as when opening turbine sump 32 (FIG. 2), optical monitor 104c' may only issue the "Target Material Error" when the high light intensity is detected for a predetermined period of time (e.g., 1 hour or more). On the other hand, if the light intensity detected by detector 144' is too low (e.g., at or near 0%), optical monitor 104c' may issue a "Light or Reflector Error" to inform the operator that light source 140' and/or reflective surface 500' may be missing or damaged. In this scenario, the entire lower housing 514', including reflective surface 500', may be missing or damaged.

Optical monitor 104c' may be combined with one or more other monitors of the present disclosure. For example, in the illustrated embodiment of FIG. 16, PCB 502' of optical monitor 104c' also supports a humidity sensor 520', which passes through upper housing 512' for exposure to the vapors in fuel delivery system 10 (FIG. 2). PCB 502' may also support a temperature sensor (not shown), which may be used to compensate for any temperature-related fluctuations in the performance of light source 140' and/or optical detector 144'.

In still yet another embodiment, monitor 104 collects spectroscopic data indicative of a corrosive environment in fuel delivery system 10. An exemplary spectrometer (not shown) operates by subjecting a liquid or vapor sample from fuel delivery system 10 to an energy source and measuring the radiative energy as a function of its wavelength and/or frequency. Suitable spectrometers include, for example, infrared (IR) electromagnetic spectrometers, ultraviolet (UV) electromagnetic spectrometers, gas chromatography-mass spectrometers (GC-MS), and nuclear magnetic resonance (NMR) spectrometers. Suitable spectrometers may detect absorption from a ground state to an excited state, and/or fluorescence from the excited state to the ground state. The spectroscopic data may be represented by a spectrum showing the radiative energy as a function of wavelength and/or frequency. It is within the scope of the present disclosure that the spectrum may be edited to hone in on certain impurities in the sample, such as acetate and acetic acid, which may cause corrosion in fuel delivery system 10, as well as sulfuric acid, which may cause odors in fuel delivery system 10. As the impurities develop in fuel delivery system 10, peaks corresponding to the impurities would form and/or grow on the spectrum. The spectrometer may share the collected data with controller 102 (FIG. 3) to signal a corrosive environment in fuel delivery system 10 when the impurity level reaches an undesirable level or changes at an undesirable rate, for example.

In still yet another embodiment, monitor 104 collects microbial data indicative of a corrosive environment in fuel delivery system 10. An exemplary microbial detector (not shown) operates by exposing a liquid or vapor sample from fuel delivery system 10 to a fluorogenic enzyme substrate, incubating the sample and allowing any bacteria in the sample to cleave the enzyme substrate, and measuring fluorescence produced by the cleaved enzyme substrate. The concentration of the fluorescent product may be directly related to the concentration of acetic acid producing bacteria (e.g., *Acetobacter, Gluconobacter, Gluconacetobacter*) in the sample. Suitable microbial detectors are commercially available from Mycometer, Inc. of Tampa, Fla. The microbial detector may share the collected data with controller 102 (FIG. 3) to signal a corrosive environment in fuel delivery system 10 when the fluorescent product concentration reaches an undesirable level or changes at an undesirable rate, for example.

To minimize the impact of other variables in monitor 104, a control sample may be provided in combination with the test sample. For example, monitor 104c of FIG. 6 may include a non-corrosive control material for comparison with the corrosive target material 142. This comparison would minimize the impact of other variables in monitor 104c, such as decreasing output from light source 140 over time.

As discussed above, control system 100 of FIG. 3 includes a remediation system 108 capable of taking at least one corrective action to remediate the corrosive environment in fuel delivery system 10. Controller 102 may activate remediation system 108 periodically (e.g., hourly, daily) in a preventative manner. Alternatively or additionally, controller 102 may activate remediation system 108 when the corrosive environment is detected by monitor 104. Various embodiments of remediation system 108 are described below with reference to FIG. 2.

In a first embodiment, remediation system 108 is configured to ventilate turbine sump 32 of fuel delivery system 10. In the illustrated embodiment of FIG. 2, remediation system 108 includes a first ventilation passageway 160 and a second ventilation or siphon passageway 170.

The first ventilation passageway 160 illustratively includes an inlet 162 in communication with the surrounding atmosphere and an outlet 164 in communication with the upper vapor space (i.e., top) of turbine sump 32. In FIG. 2, the first ventilation passageway 160 is positioned in lid 38 of turbine sump 32, but this position may vary. A control valve 166 (e.g., bulkhead-style vacuum breaker, check valve) may be provided along the first ventilation passageway 160. Control valve 166 may be biased closed and opened when a sufficient vacuum develops in turbine sump 32, which allows air from the surrounding atmosphere to enter turbine sump 32 through the first ventilation passageway 160.

The second ventilation or siphon passageway 170 is illustratively coupled to a siphon port 26 of pump 20 and includes an inlet 172 positioned in the lower vapor space (i.e., middle) of turbine sump 32 and an outlet 174 positioned in storage tank 16. A control valve 176 (e.g., automated valve, flow orifice, check valve, or combination thereof) may be provided in communication with controller 102 (FIG. 3) to selectively open and close the second ventilation passageway 170. Other features of the second ventilation passageway 170 not shown in FIG. 2 may include a restrictor, a filter, and/or one or more pressure sensors.

When pump 20 is active (i.e., turned on) to dispense fuel product 14, pump 20 generates a vacuum at siphon port 26. The vacuum from pump 20 draws vapor (e.g., fuel/air mixture) from turbine sump 32, directs the vapor to the manifold of pump 20 where it mixes with the circulating liquid fuel flow, and then discharges the vapor into storage tank 16 through the second ventilation passageway 170. As the vacuum in turbine sump 32 increases, control valve 166 may also open to draw fresh air from the surrounding atmosphere and into turbine sump 32 through the first ventilation passageway 160. When pump 20 is inactive (i.e., turned off), controller 102 (FIG. 3) may close control valve 176 to prevent back-flow through the second ventilation passageway 170. Additional information regarding the second ventilation passageway 170 is disclosed in U.S. Pat. No. 7,051,579, the disclosure of which is expressly incorporated herein by reference in its entirety.

The vapor pressure in turbine sump 32 and/or storage tank 16 may be monitored using the one or more pressure sensors (not shown) and controlled. To prevent over-pressurization of storage tank 16, for example, the vapor flow into storage tank 16 through the second ventilation passageway 170 may be controlled. More specifically, the amount and flow rate of vapor pulled into storage tank 16 through the second ventilation passageway 170 may be limited to be less than the amount and flow rate of fuel product 14 dispensed from storage tank 16. In one embodiment, control valve 176 may be used to control the vapor flow through the second ventilation passageway 170 by opening the second ventilation passageway 170 for limited durations and closing the second ventilation passageway 170 when the pressure sensor detects an elevated pressure in storage tank 16. In another embodiment, the restrictor (not shown) may be used to limit the vapor flow rate through the second ventilation passageway 170 to a level that will avoid an elevated pressure in storage tank 16.

Other embodiments of the first ventilation passageway 160 are also contemplated. In a first example, the first ventilation passageway 160 may be located in the interstitial space between a primary pipe and a secondary pipe (e.g., XP Flexible Piping available from Franklin Fueling Systems Inc. of Madison, Wis.) using a suitable valve (e.g., APT™ brand test boot valve stems available from Franklin Fueling Systems Inc. of Madison, Wis.). In a second example, the first ventilation passageway 160 may be a dedicated fresh air line into turbine sump 32. In a third example, the first ventilation passageway 160 may be incorporated into a pressure/vacuum (PV) valve system. Traditional PV valve systems communicate with storage tank 16 and the surrounding atmosphere to help maintain proper pressure differentials therebetween. One such PV valve system is disclosed in U.S. Pat. No. 8,141,577, the disclosure of which is expressly incorporated herein by reference in its entirety. In one embodiment, the PV valve system may be modified to pull fresh air through turbine sump 32 on its way into storage tank 16 when the atmospheric pressure exceeds the ullage pressure by a predetermined pressure differential (i.e., when a sufficient vacuum exists in storage tank 16). In another embodiment, the PV valve system may be modified to include a pair of tubes (e.g., coaxial tubes) in communication with the surrounding atmosphere, wherein one of the tubes communicates with storage tank 16 to serve as a traditional PV vent when the ullage pressure exceeds the atmospheric pressure by a predetermined pressure differential, and another of the tubes communicates with turbine sump 32 to introduce fresh air into turbine sump 32.

Other embodiments of the second ventilation passageway 170 are also contemplated. In a first example, instead of venting the fuel/air mixture from turbine sump 32 into storage tank 16 as shown in FIG. 2, the mixture may be directed through a filter and then released into the atmosphere. In a second example, instead of using siphon port 26 as the vacuum source for the second ventilation passageway 170 as shown in FIG. 2, the vacuum source may be an existing vacuum pump in fuel delivery system 10 (e.g., 9000 Mini-Jet available from Franklin Fueling Systems Inc. of Madison, Wis.), a supplemental and stand-alone vacuum pump, or a vacuum created by displaced fuel in storage tank 16 and/or fuel delivery line 18. In one embodiment, and as discussed above, the second ventilation passageway 170 may be incorporated into the PV valve system to pull fresh air through turbine sump 32 and then into storage tank 16 when fuel is displaced from storage tank 16. In another embodiment, the second ventilation passageway 170 may communicate with an in-line siphon port on fuel delivery line 18 to pull air from turbine sump 32 when fuel is displaced along fuel delivery line 18.

In a second embodiment, remediation system 108 is configured to irradiate bacteria in turbine sump 32 of fuel delivery system 10. In the illustrated embodiment of FIG. 2, a first radiation source 180 is positioned on an outer wall of turbine sump 32, and a second radiation source 180' is positioned in the ullage of storage tank 16. Exemplary radiation sources 180, 180' include ultraviolet-C (UV-C) light sources. When activated by controller 102 (FIG. 3), radiation sources 180, 180' may irradiate and destroy any bacteria in turbine sump 32 and/or storage tank 16, especially acetic acid producing bacteria (e.g., *Acetobacter, Gluconobacter, Gluconacetobacter*).

Figure 11:
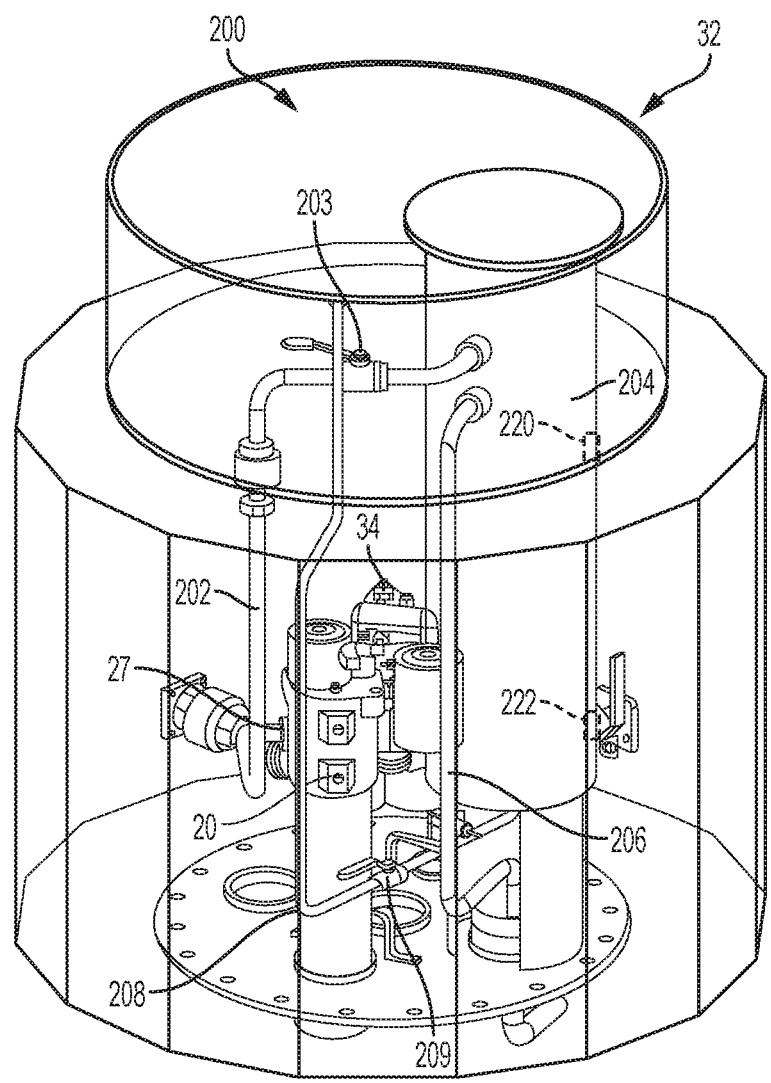
FIG. 11 is a perspective view of the turbine sump having a water filtration system.

In a third embodiment, remediation system 108 is configured to filter water from fuel product 14. An exemplary water filtration system 200 is shown in FIG. 11 and is located together with pump 20 in turbine sump 32 above storage tank 16 (FIG. 1). The illustrative water filtration system 200 includes a fuel inlet passageway 202 coupled to port 27 of pump 20, a water filter 204, a fuel return passageway 206 from the upper end of water filter 204, and a water removal passageway 208 from the lower end of water filter 204. The port 27 of pump 20 may be located upstream of leak detector 34 and its associated check valve (not shown) such that the water filtration system 200 avoids interfering with leak detector 34.

Water filter 204 is configured to separate water, including emulsified water and free water, from fuel product 14. Water filter 204 may also be configured to separate other impurities from fuel product 14. Water filter 204 may operate by coalescing the water into relatively heavy droplets that separate from the relatively light fuel product 14 and settle at the lower end of water filter 204. Incoming fuel pressure drives fuel radially outwardly through the sidewall of filter element 207 (FIG. 15), while any water that is separated from the fuel is driven downwardly through the bottom of filter element 207 and falls by gravity to the bottom of the filter housing. Exemplary water filters 204 are available from DieselPure Inc. Such water filters 204 may reduce the water content of fuel product 14 to 200 ppm or less, according to the SAE J1488 ver.2010 test method.

Figure 14:
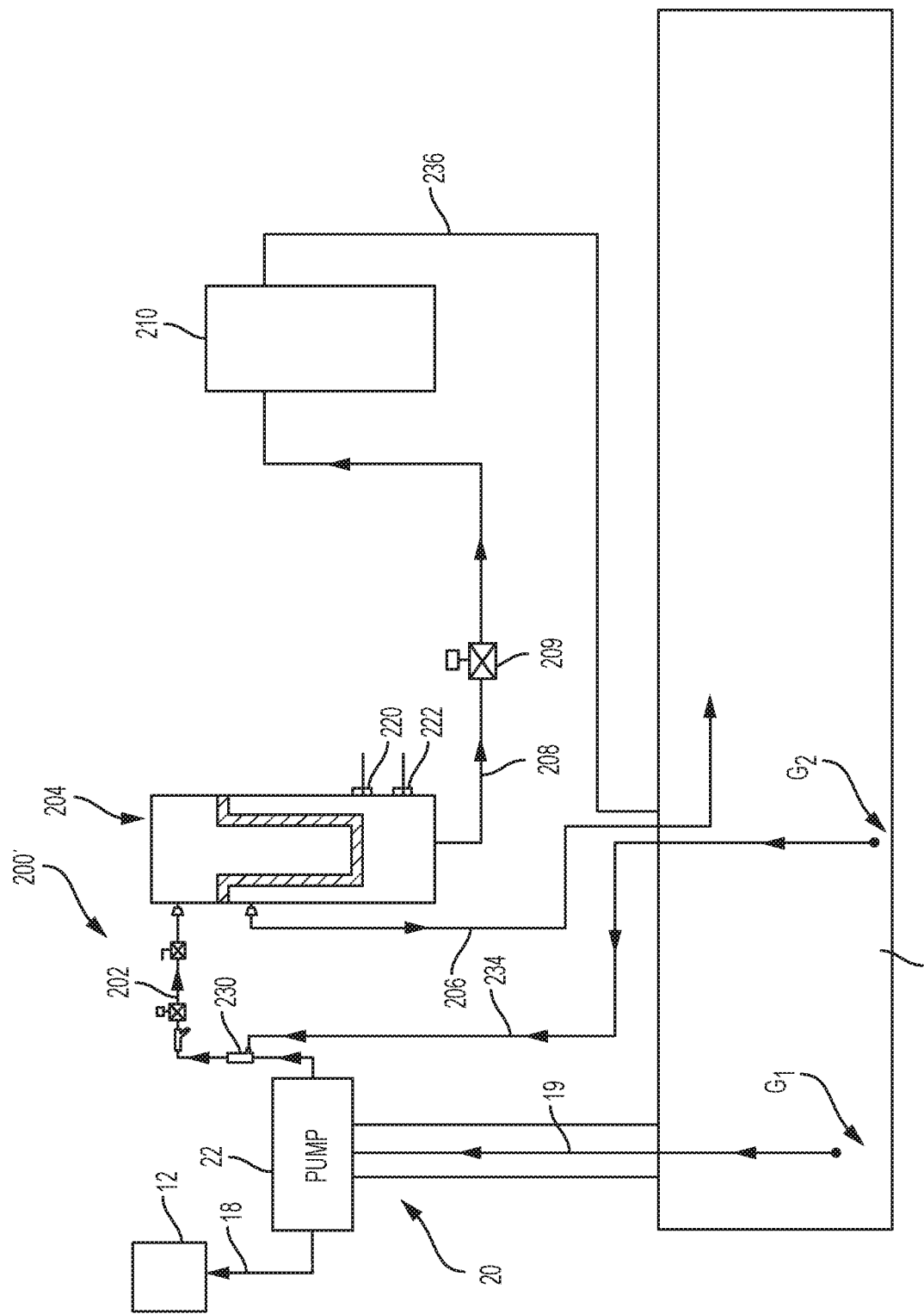
FIG. 14 is a schematic view of another exemplary water filtration system utilizing continuous filtration by eduction.
Figure 15:
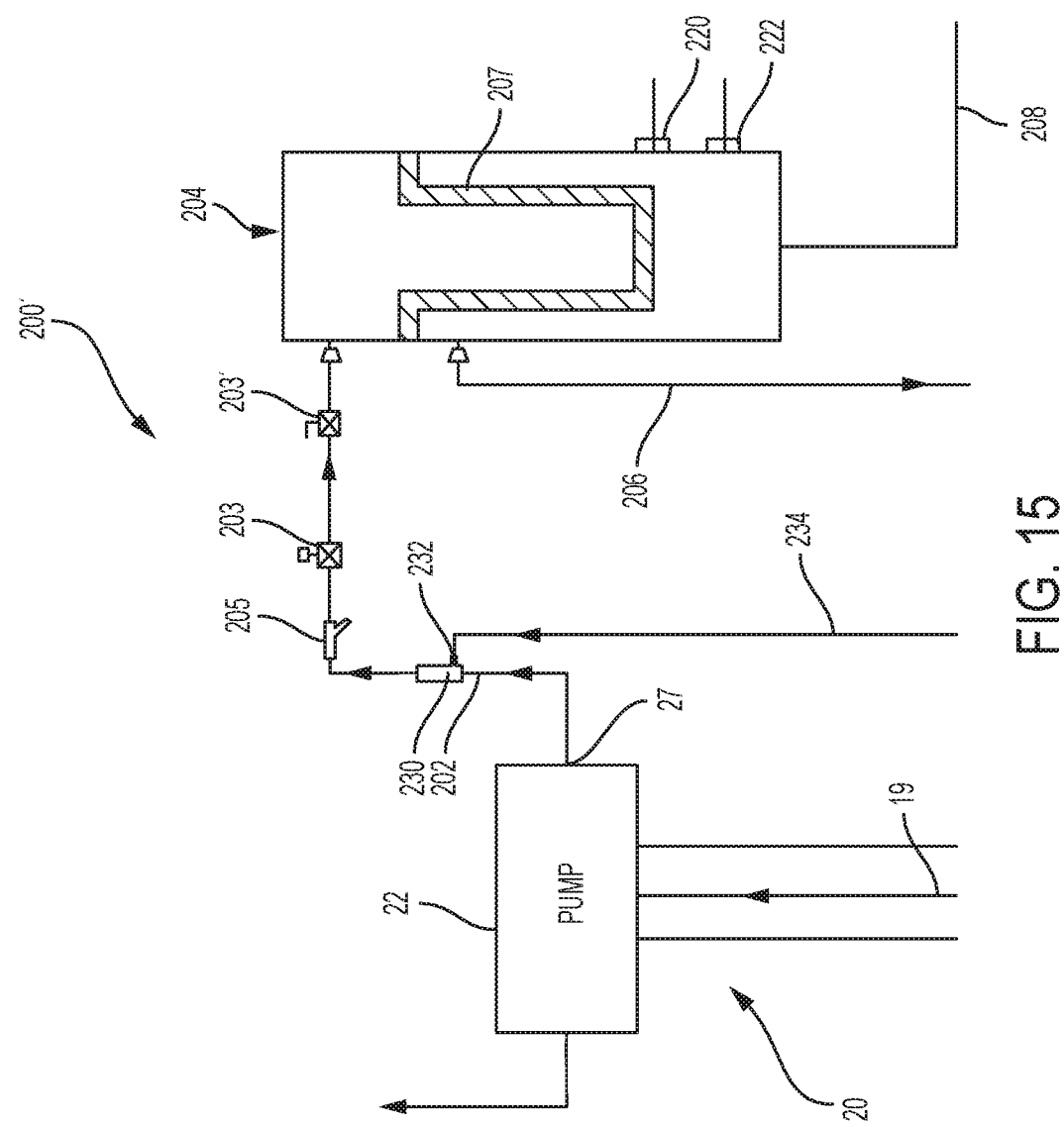
FIG. 15 is an enlarged portion of the schematic view of FIG. 14, illustrating the components of the water filtration system.
Figure 16:
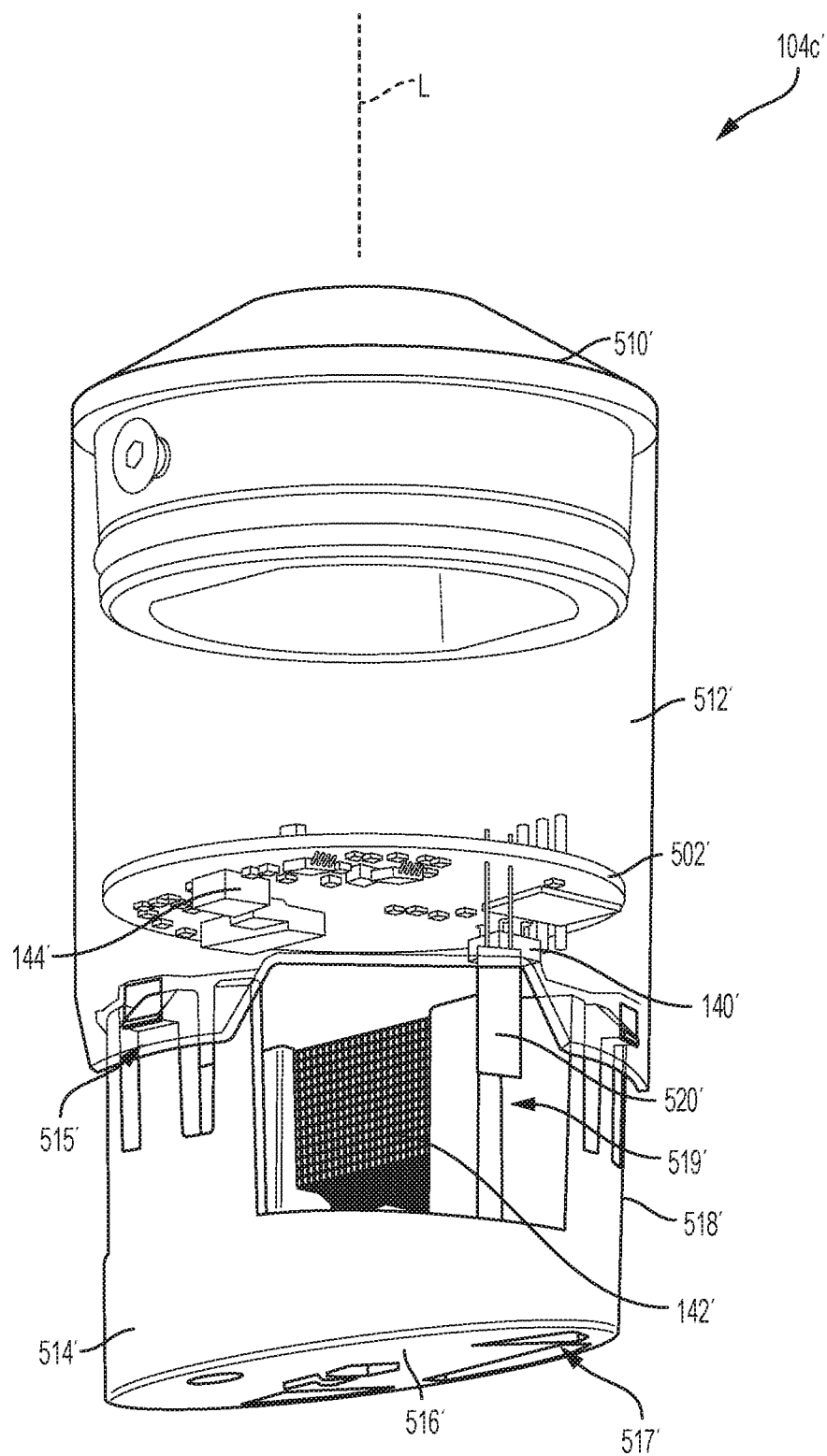
FIG. 16 is a perspective view of another exemplary optical monitor including an upper housing with a light source and an optical detector and a lower housing with a corrosive target material and a reflective surface.
Figure 18:
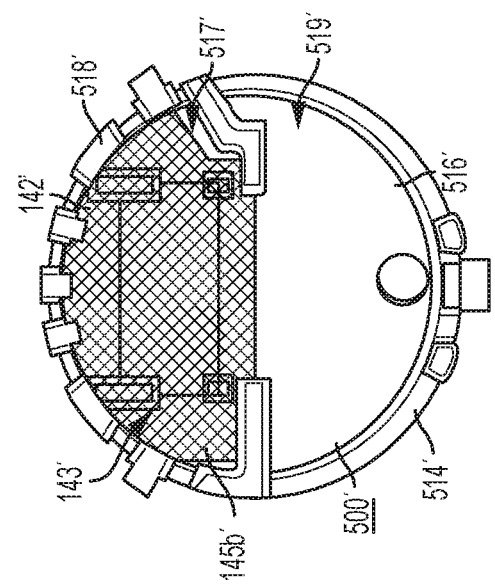
FIG. 18 is a top plan view of the lower housing and the corrosive target material of FIG. 16.
Figure 17:
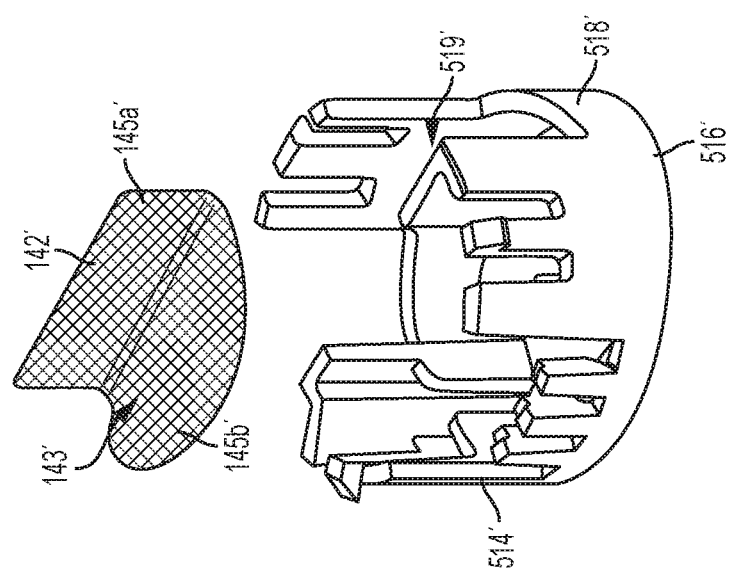
FIG. 17 is an exploded perspective view of the lower housing and the corrosive target material of FIG. 16.

The illustrative water filtration system 200 also includes one or more inlet valves 203 to selectively open and close the fuel inlet passageway 202 and one or more drain valves 209 to selectively open and close the water removal passageway 208. In certain embodiments, valves 203, 209 are solenoid valves that are controlled through controller 102. In other embodiments, valves 203, 209 are manual valves that are manually controlled by a user. In the embodiment of FIGS. 14-15, inlet solenoid valve 203 is provided downstream of strainer 205, which includes a mesh screen to protect valve 203 from exposure to solid sediment. A further manual ball valve 203' is provided downstream of solenoid valve 203 for manual on/off control of the illustrated filtration system 200', the details of which are further discussed below.

In operation, water filtration system 200 circulates fuel product 14 through water filter 204. Water filtration system 200 may operate at a rate of approximately 15 to 20 gallons per minute (GPM), for example. When pump 20 operates with inlet valve 203 open, pump 20 directs some or all of fuel product 14 from storage tank 16, through port 27 of pump 20, through the open fuel inlet passageway 202, and through water filter 204. If a customer is operating dispenser 12 (FIG. 1) during operation of water filtration system 200, pump 20 may direct a portion of the fuel product 14 to dispenser 12 via the delivery line 18 (FIG. 1) and another portion of the fuel product 14 to water filter 204 via the fuel inlet passageway 202. It is also within the scope of the present disclosure that the operation of water filtration system 200 may be interrupted during operation of dispenser 12 by temporarily closing inlet valve(s) 203 and/or 203' to water filter 204. As shown schematically in FIG. 14, water filter 204 may produce a clean or filtered fuel product 14 near the upper end of water filter 204 and a separated water product, which may be a water/oil mixture, near the lower end of water filter 204.

The clean or filtered fuel product 14 that has risen to the upper end of water filter 204 may be returned continuously to storage tank 16 via the fuel return passageway 206. The filtered fuel product 14 may be returned to storage tank 16 in a dispersed and/or forceful manner that promotes circulation in storage tank 16, which prevents debris from settling in storage tank 16 and promotes filtration of such debris. By returning the filtered fuel product 14 to storage tank 16, water filtration system 200 may reduce the presence of water and avoid formation of a corrosive environment in fuel delivery system 10 (FIG. 1), including storage tank 16 and/or sump 32 of fuel delivery system 10. Water filtration system 200 may be distinguished from an in-line system that delivers a filtered fuel product to dispenser 12 (FIG. 1) solely to protect a consumer's vehicle.

Figure 12:
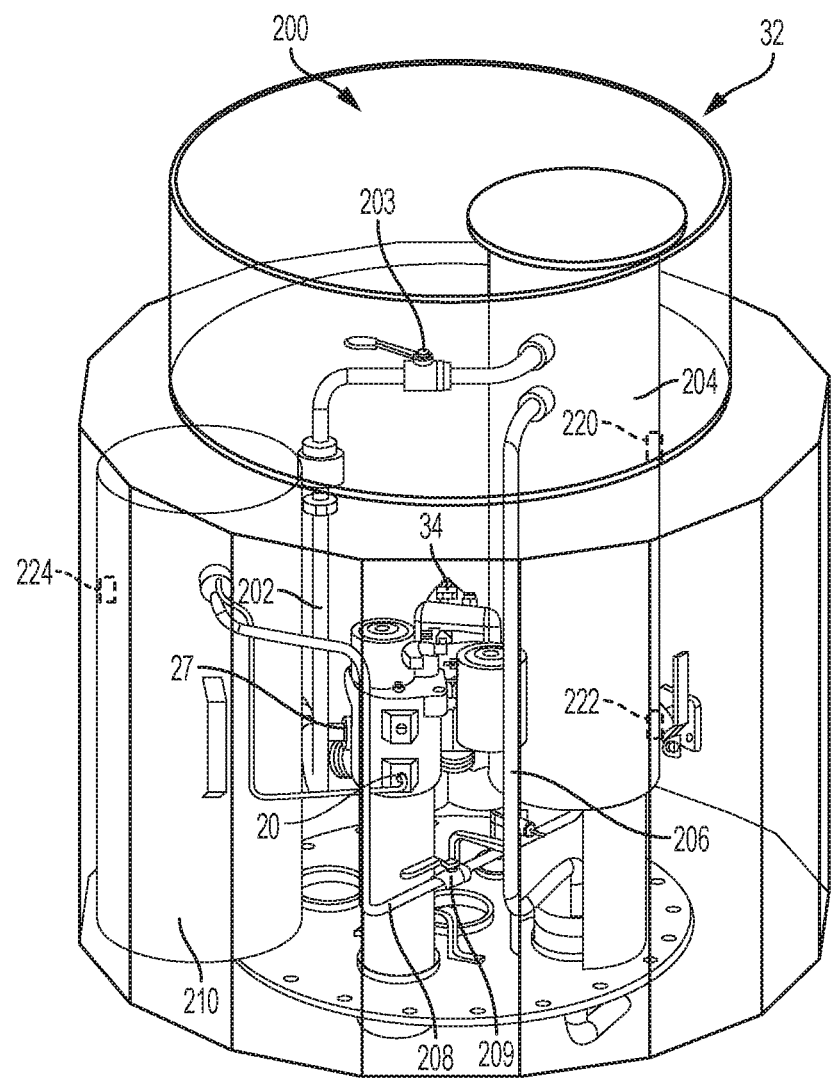
FIG. 12 is a perspective view of the turbine sump having a water filtration system similar to FIG. 11 and also including a water storage tank.

The separated water product that has settled at the lower end of water filter 204 may be drained via the water removal passageway 208 when drain valve 209 is open. The separated water product may be directed out of turbine sump 32 and above grade for continuous removal, as shown in FIG. 11. Alternatively, the separated water product may be directed via passageway 208 to a storage tank 210 inside turbine sump 32 for batch removal when necessary, as shown in FIGS. 12 and 14. If the separated water product is a water/oil mixture, the separated water product may be subjected to further processing to remove any oil from the remaining water. For example, a selective absorbent, such as the Smart Sponge® available from AbTech Industries Inc., may be used to absorb and remove any oil from the remaining water.

Referring to FIG. 14, storage tank 210 further includes a vent line 236 operable to vent the headspace above the separated water product as the level within tank 210 increases. In an exemplary embodiment, vent line 236 may be routed to the headspace above fuel product 14 within underground storage tank 16, such that any treatment or capture of the vapor within tank 210 may be routed through existing infrastructure used for treatment/capture of fuel vapor within tank 16. Alternatively, tank 210 may be vented to a dedicated space as required or desired for a particular application.

The illustrative water filtration systems 200, 200' of FIGS. 11, 12, 14 and 15 include a high-level water sensor 220 and a low-level water sensor 222 operably connected to water filter 204. The water sensors 220 and 222 may be capacitance sensors capable of distinguishing fuel product 14 from water. The high-level water sensor 220 may be located beneath the entry into fuel return passageway 206 to prevent water from entering fuel return passageway 206. The illustrative water filtration system 200 of FIG. 12 further includes a high-level water sensor 224 in storage tank 210. The high-level water sensor 224 may be an optical sensor capable of distinguishing the separated water product from air. Sensors 220, 222, and 224 may be low-power devices suitable for operation in turbine sump 32. In one exemplary embodiment, filter 204 may have a water capacity of about 2.75 liters (0.726 gallons) between the levels of sensors 220, 222.

Turning to FIG. 14, water filtration system 200' is shown. Water filtration system 200' is similar to filtration system 200 described above and includes several components and features in common with system 200 as indicated by the use of common reference numbers between systems 200, 200'. However, water filtration system 200' further includes eductor 230 in fuel inlet passageway 202 which operates to effect continuous fuel filtration during operation of pump 20, while also allowing for normal operation of fuel dispenser 12 served by pump 20 as further described below.

As fuel is withdrawn from tank 16 by operation of pump 20, a portion of the fuel which would otherwise be delivered to dispenser 12 via delivery line 18 is instead diverted to fuel inlet passageway 202. In an exemplary embodiment, this diverted flow may be less than 15 gallons/minute, such as between 10 and 12 gallons/minute. This diverted flow of pressurized fuel passes through eductor 230, as shown in FIGS. 14 and 15, which is a venturi device having a constriction in the cross-sectional area of the eductor flow path. As the flow of fuel passes through this construction, a negative pressure (i.e., a vacuum) is formed at vacuum port 232 (FIG. 15), which may be separate flow tube terminating in an aperture formed in the sidewall of eductor 230 downstream of the constriction.

Filtration uptake line 234 is connected to vacuum port 232 and extends downwardly into tank 16, such that filtration uptake line 234 draws fuel from the bottom of tank 16. In an exemplary embodiment, gap $G_2$ between the inlet of line 234 and the bottom surface of tank 16 is zero or near-zero, such that all or substantially all water or sediment which may be settled at the bottom of tank 16 is accessible to filtration uptake line 234. For example, line 234 may be a rigid or semi-rigid tube with an inlet having an angled surface formed, e.g., by a cut surface forming a 45-degree angle with the longitudinal axis of the tube. This angled surface forms a point at the inlet of line 234 which can be lowered into abutting contact with the lower surface of tank 16, while the open passageway exposed by the angled surface allows the free flow of fuel into line 234. Other inlet configuration may also be used for line 234, including traditional inlet openings close to, but not abutting, the lower surface of the tank.

By contrast to the zero or near-zero gap $G_2$ for filtration uptake line 234, a larger gap $G_1$ is formed between the intake of fuel uptake line 19 and the bottom surface of tank 16. For example, the intake opening to submersible pump 24 (FIG. 1) may be about 4-6 inches above the lower surface of tank 16. Where the pump is located above fuel product 14, the intake opening into fuel uptake line may instead be about 4-6 inches above the lower surface of tank 16. This elevation differential reflected by gaps $G_1$ and $G$ ensures that any water or contaminated fuel settled at the bottom of tank 16 will be taken up by filtration uptake line 234 rather than fuel uptake line 19. At the same time, the relatively high elevation of the intake opening serving delivery line 18 ensures that any accumulation of contaminated fuel will be safely within gap $G_1$, such that only clean fuel will be delivered to dispenser 12. In this way, filtration system 200' simultaneously remediates contamination and protects against uptake of any contaminated fuel that may exist in tank 16, thereby providing "double protection" against delivery of contaminated fuel to dispenser 12.

The illustrative filtration system 200' also achieves this dual mitigation/prevention functionality with low-maintenance operation, by using eductor 230 to convert the operation of pump 20 into the motive force for the operation of system 200'. In particular, a single only pump 20 used in conjunction with system 200' both provides clean fuel to dispenser(s) 12 via delivery line 18, while also ensuring that any accumulation of contaminated fuel at the bottom of tank 16 is remediated by uptake into filtration line 234 and subsequent delivery to filter 204. The lack of a requirement of extra pumping capacity lowers both initial cost and running costs. Moreover, the additional components of system 200', such as eductor 230, filter 204, valves 203, 209 and water tank 210, all require little to no regular maintenance.

Filtration system 200' also achieves its dual mitigation/prevention function in an economically efficient manner by using an existing pump to power the filtration process, while avoiding the need for large-capacity filters. As described in detail above, filtration system 200' is configured to operate in conjunction with the normal use of fuel delivery system 10 (FIG. 1), such that the filtration occurs whenever dispensers 12 are used to fuel vehicles. This ensures that filtration system 200' will operate with a frequency commensurate with the frequency of use of fuel delivery system 10. This high frequency of operation allows filter 204 to be specified with a relatively small filtration capacity for a given system size, while ensuring that filtration system 200' retains sufficient overall capacity to mitigate even substantial contamination. For example, a throughput of 10-12 gallons/minute through filter 204 may be sufficient to treat all the fuel contained in a tank 16 sized to serve 6-8 fuel dispensers 12 (FIG. 1) with each dispenser 12 capable of delivering 15-20 gallons of clean fuel per minute. In this system sizing example, eductor 230 may be sized to deliver 0.1-0.3 gallons per minute of fluid via filtration uptake line 234 with a maximum vertical lift of 15 feet, using a flow through fuel inlet passageway 202 of 10-12 gallons per minute at an inlet pressure of about 30 PSIG (resulting in a pressure of at least 5 PSIG at the outlet of eductor 230).

Although the illustrative filtration system 200' uses eductor 230 to draw the contaminated fuel from the bottom of tank 16, other equipment may be used to perform this operation, such as another type of venturi device or a supplemental pump (in addition to pump 22).

Figure 13:
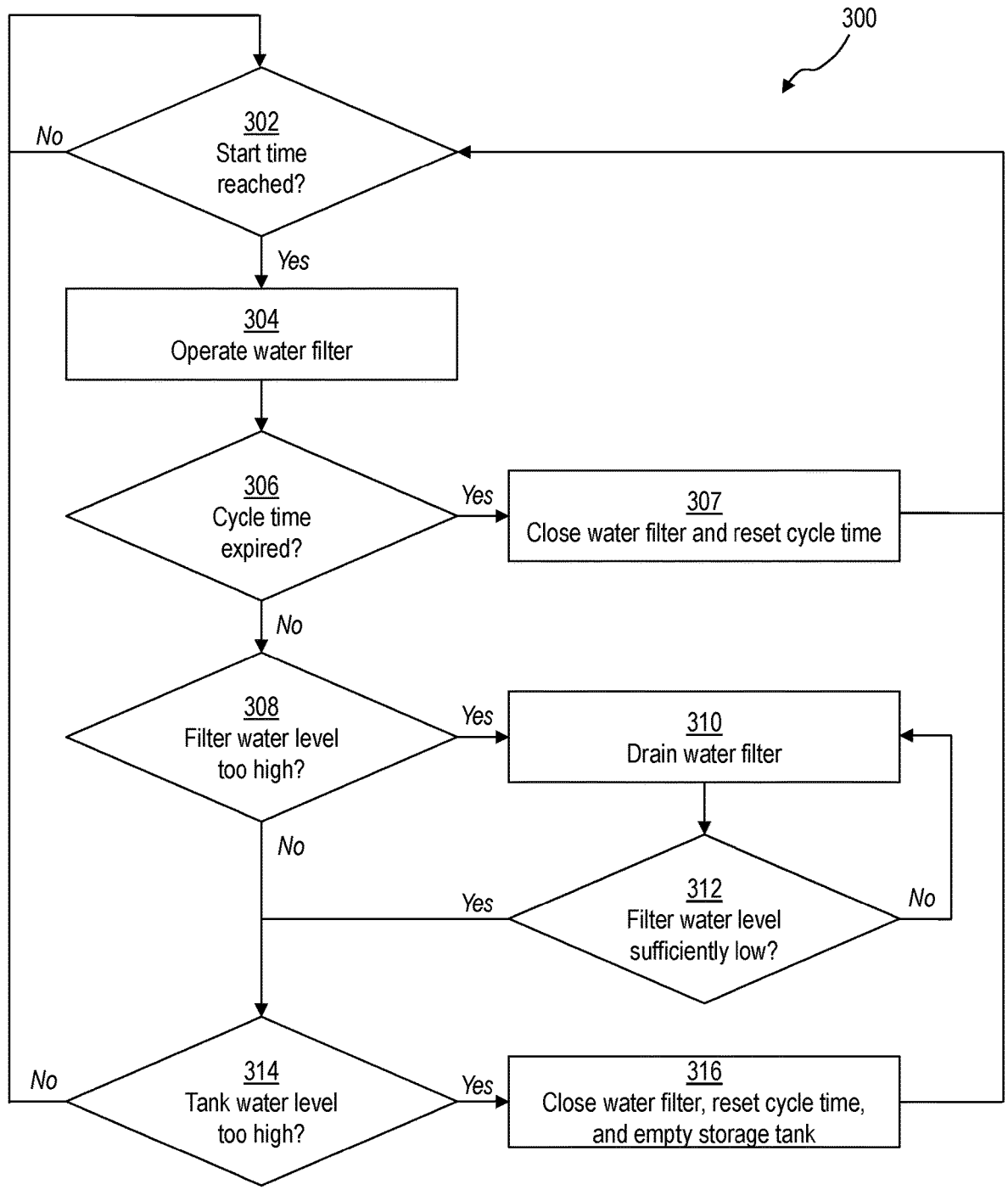
FIG. 13 shows an exemplary method for operating the water filtration system.

Referring next to FIG. 13, an exemplary method 300 is disclosed for operating water filtration systems 200, 200'. Method 300 may be performed using controller 102 (FIG. 3). Method 300 is described below with reference to the illustrative water filtration system 200 of FIG. 12, though the disclosed method is also applicable to system 200'.

In step 302 of method 300, controller 102 determines whether a predetermined start time has been reached. The start time may occur at a desired time, preferably outside of high-demand fuel dispensing hours (e.g., 4:30 to 7:30 AM), and with a desired frequency. For example, the start time may occur daily at about 8:00 PM. When the start time of step 302 is reached, method 300 continues to step 304. It is also within the scope of the present disclosure that method 300 may be initiated based on an input from one or more monitors 104 (FIG. 3). It is further within the scope of the present disclosure that method 300 may be initiated only when a certain minimum level of fuel product 14 is present in storage tank 16, such as about 20 to 30 inches of fuel product 14, more specifically about 24 inches of fuel product 14.

In step 304 of method 300, controller 102 operates water filter 204 to filter fuel product 14. As discussed above, this filtering step 304 may involve opening inlet valve 203 of fuel inlet passageway 202 and activating pump 20. After passing through water filter 204, the filtered fuel product 14 may be returned continuously to storage tank 16 via fuel return passageway 206.

In step 306 of method 300, controller 102 determines whether a predetermined cycle time has expired. The cycle time may vary. For example, the cycle time may be about 1-10 hours, more specifically about 7-9 hours, and more specifically about 8 hours. If the cycle time has expired, method 300 continues to step 307, in which controller 102 closes inlet valve 203 of fuel inlet passageway 202 to water filter 204 and resets the cycle time before returning to step 302 to await a new start time. If the cycle time has not yet expired, method 300 continues to step 308.

In step 308 of method 300, controller 102 determines whether a water level in water filter 204 is too high. Step 308 may involve communicating with the high-level water sensor 220 in water filter 204. If the high-level water sensor 220 detects water (i.e., activates), method 300 continues to steps 310 and 312. If the high-level water sensor 220 does not detect water (i.e., deactivates), method 300 skips steps 310 and 312 and continues to step 314.

In step 310 of method 300, controller 102 drains the separated water product from water filter 204. As discussed above, this draining step 310 may involve opening drain valve 209 of water removal passageway 208. From step 310, method continues to step 312.

In step 312 of method 300, controller 102 determines whether a water level in water filter 204 is sufficiently low. Step 312 may involve communicating with the low-level water sensor 222 in water filter 204. If the low-level water sensor 222 still detects water (i.e., activates), method 300 returns to step 310 to continue draining water filter 204. Once the low-level water sensor 222 no longer detects water (i.e., deactivates), method 300 continues to step 314. Controller 102 may initiate an alarm if the draining step 310 is performed for a predetermined period of time without deactivating the low-level water sensor 222. Controller 102 may also initiate an alarm if a discrepancy exists between the high-level water sensor 220 and the low-level water sensor 222, specifically if the high-level water sensor 220 detects water (i.e., activates) but the low-level water sensor 222 does not detect water (i.e., deactivates).

In step 314 of method 300, controller 102 determines whether a water level in storage tank 210 is too high. Step 314 may involve communicating with the high-level water sensor 224 in storage tank 210. Step 314 may also involve calculating the volume of water contained in storage tank 210 based on prior draining steps 310 from water filter 204. This volume calculation may involve logging the number of draining steps 310 from water filter 204 triggered by the high water-level sensor 220 and determining the known volume of water drained between sensors 220 and 222 during each draining step 310. If the high-level water sensor 224 does not detect water (i.e., deactivates) or the calculated water volume inside storage tank 210 is lower than a predetermined limit, method 300 returns to step 304 to continue operating water filter 204. If the high-level water sensor 224 detects water (i.e., activates) or the calculated water volume inside storage tank 210 reaches the predetermined limit, method 300 continues to step 316.

In step 316 of method 300, controller 102 initiates an alarm or sends another communication requiring storage tank 210 to be emptied and replaced. Controller 102 also closes inlet valve 203 of fuel inlet passageway 202 and resets the cycle time. After storage tank 210 is emptied and replaced, controller 102 returns to step 302 to await a new start time.

In a fourth embodiment, remediation system 108 is configured to control the humidity in turbine sump 32 of fuel delivery system 10. In the illustrated embodiment of FIG. 2, remediation system 108 includes a desiccant 400 (e.g., calcium chloride, silica gel) that is configured to adsorb water from the atmosphere in turbine sump 32. Desiccant 400 may be removably coupled to turbine sump 32, such as being detachably suspended from lid 38 of turbine sump 32. In this embodiment, monitor 104'''' may be a humidity sensor that is configured to measure the humidity in the vapor space of turbine sump 32. Monitor 104'''' may also be configured to measure the temperature in the vapor space of turbine sump 32. The humidity and/or temperature data may be communicated to controller 102 (FIG. 3). When the humidity level increases above a predetermined level (e.g., 40%), output 106 may instruct the operator to inspect turbine sump 32 and/or to replace desiccant 400.

The above-described embodiments of remediation system 108 may be provided individually or in combination, as shown in FIG. 2. Thus, remediation system 108 may be configured to ventilate turbine sump 32 of fuel delivery system 10, irradiate bacteria in turbine sump 32 of fuel delivery system 10, operate water filtration system 200, and/or control the humidity in turbine sump 32 of fuel delivery system 10.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

EXAMPLES

1. Example 1: Degradation of Transmitted Light Intensity in Corrosive Environment Various plain steel samples were prepared as summarized in Table 1 below. Each sample was cut into a 1-inch square.

TABLE 1

| No. | Description | Dimensions |
| --- | --- | --- |
| 1 | Fine wire mesh | 60 × 60 mesh, 0.0075" wire diameter |
| 2 | Thick wire mesh | 14 × 14 mesh, 0.035" wire diameter |
| 3 | Perforated sheet | 0.033" hole diameter |
| 4 | Fine wire mesh | 30 × 30 mesh, 0.012" wire diameter |
| 5 | Perforated sheet | 0.024" hole diameter |

The samples were placed in a sealed glass container together with a 5% acetic acid solution. The samples were suspended on a non-corrosive, stainless steel platform over the acetic acid solution for exposure to the acetic acid vapor in the container. Select samples were removed from the container after about 23, 80, and 130 hours. Other samples were reserved as control samples.

Figure 8:
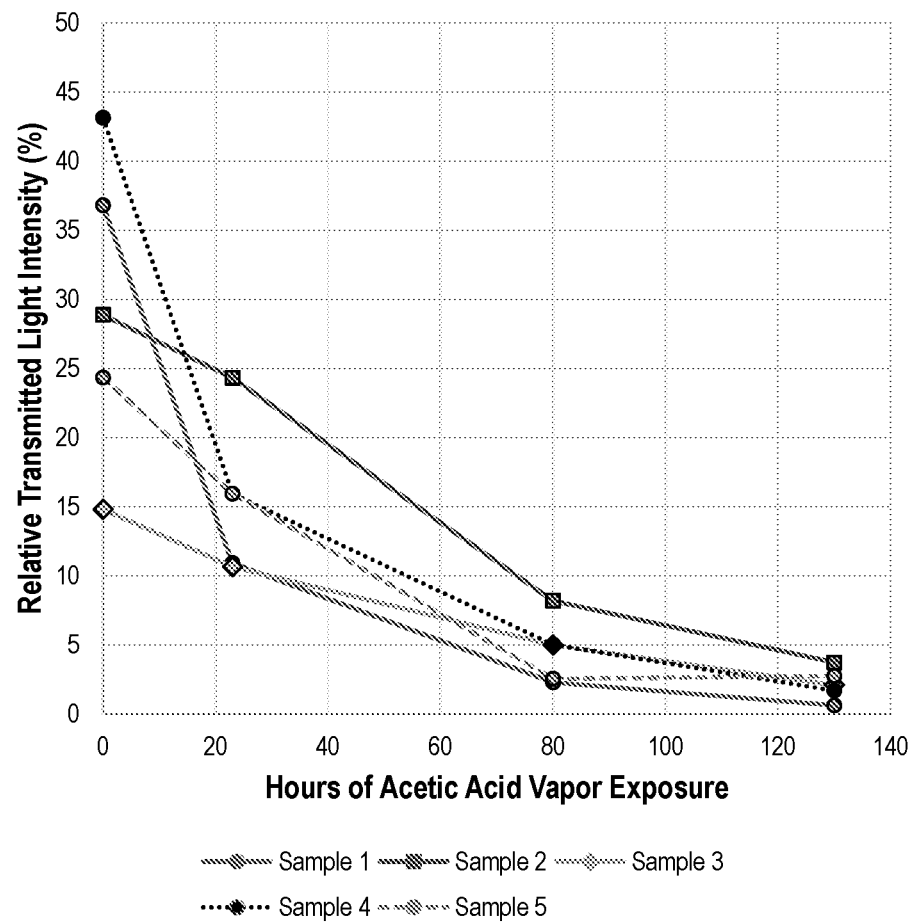
FIG. 8 is a graphical representation of the relative transmitted light intensity through each sample of Example 1 over time.
Figure 9:
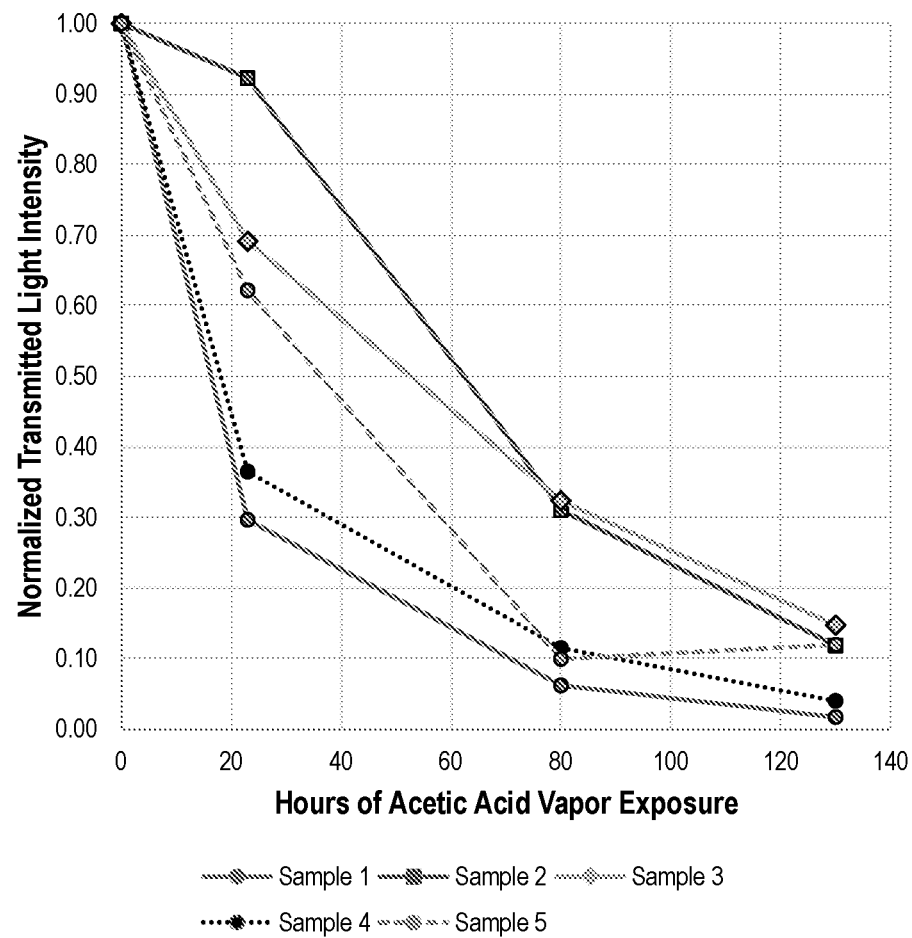
FIG. 9 is a graphical representation of the normalized transmitted light intensity through each sample of Example 1 over time.

Each sample was placed inside a holder and illuminated with a LED light source inside a tube to control light pollution. An ambient light sensor from ams AG was used to measure the intensity of the light passing through each sample. The results are presented in FIGS. 7-9. FIG. 7 includes photographs of the illuminated samples themselves. FIG. 8 is a graphical representation of the relative light intensity transmitted through each sample over time. FIG. 9 is a graphical representation of the normalized light intensity transmitted through each sample over time, with an intensity of 1.00 assigned to each control sample. As shown in FIGS. 7-9, all of the samples exhibited increased corrosion and decreased light transmission over time. The fine wire mesh samples (Sample Nos. 1 and 4) exhibited the most significant corrosion over time.

Figure 10:
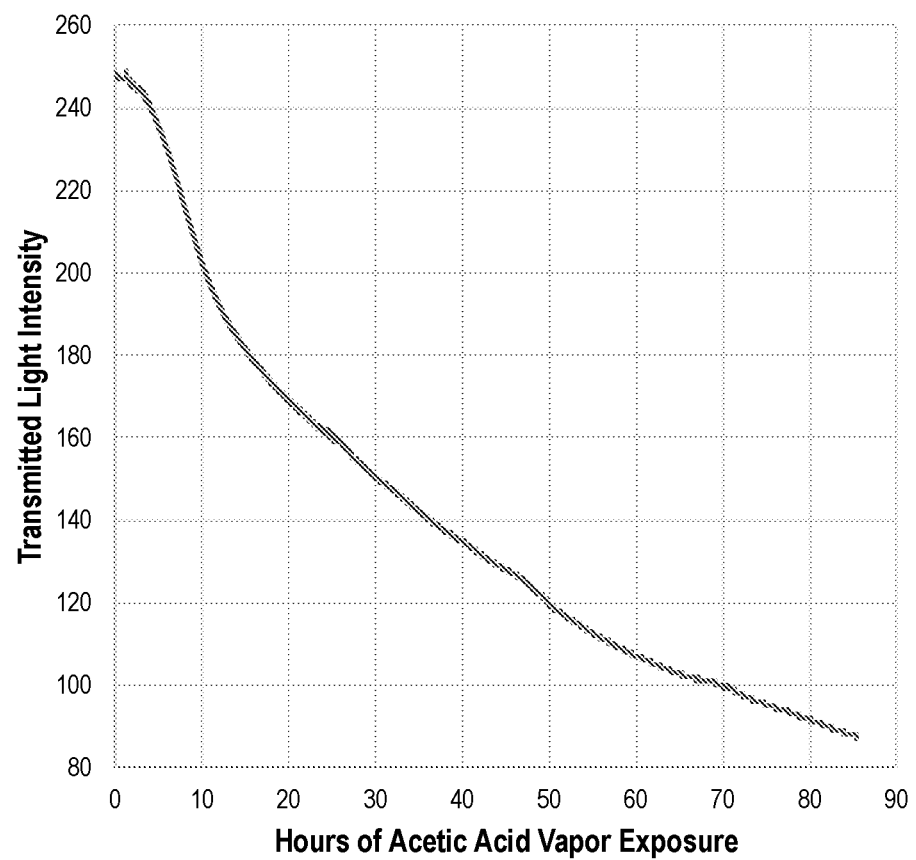
FIG. 10 is a graphical representation of the transmitted light intensity through the corrosive sample tested in Example 2 over time.

2. Example 2: Real-Time Degradation of Transmitted Light Intensity in Corrosive Environment Sample No. 4 of Example 1 was placed inside a sealed plastic bag together with a paper towel that had been saturated with a 5% acetic acid solution. The sample was subjected to illumination testing in the same manner as Example 1, except that the sample remained inside the sealed bag during testing. The results are presented in FIG. 10, which is a graphical representation of the actual light intensity transmitted through the sample over time. Like Example 1, the sample exhibited increased corrosion and decreased light transmission over time.

3. Example 3: Humidity Control with Desiccant

A turbine sump having a volume of 11.5 cubic feet and a stable temperature between about 65° F. and 70° F. was humidified to about 95% using damp rags. The rags were then removed from the humidified turbine sump. A desiccant bag was placed inside the humidified turbine sump, which was then sealed closed. The desiccant bag contained 125 g of calcium chloride with a gelling agent to prevent formation of aqueous calcium chloride.

Figure 20:
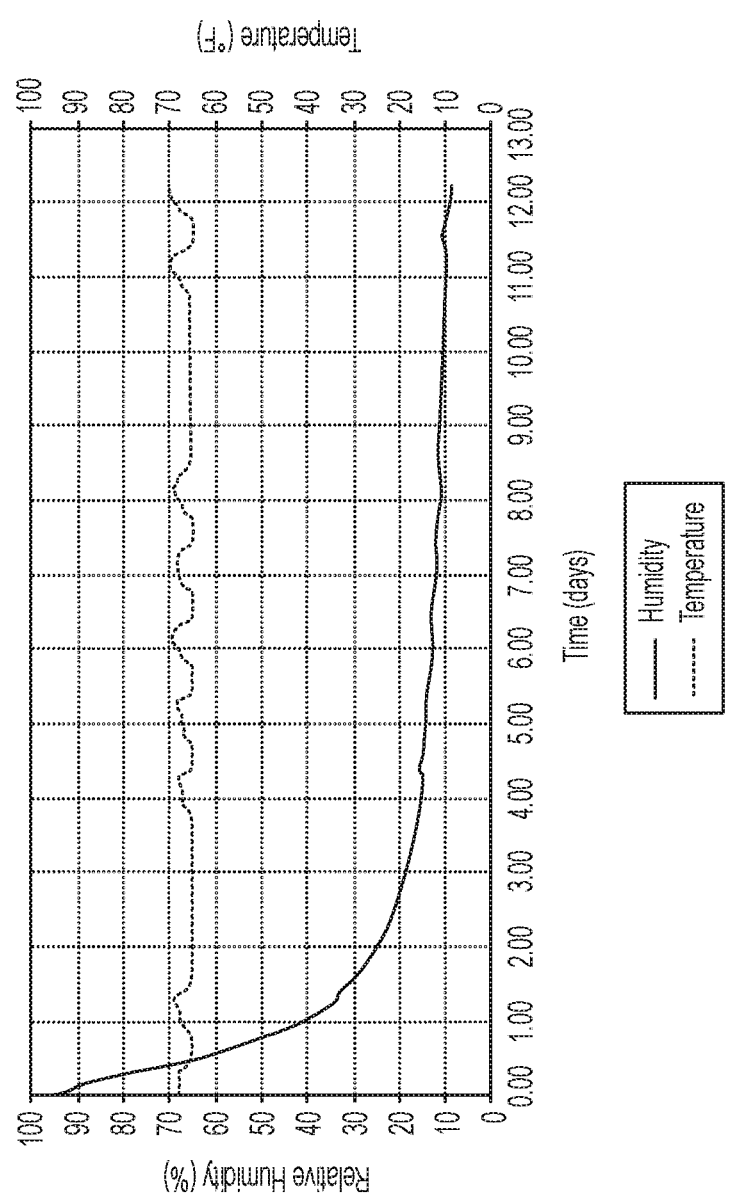
FIG. 20 is a graphical representation of the relative humidity and temperature over time in a turbine sump with a desiccant.

The relative humidity and temperature in the turbine sump were measured over time, as shown in FIG. 20. After 1 day, the desiccant had adsorbed enough moisture to decrease the relative humidity to about 40%. After 3 days, the desiccant had adsorbed enough moisture to decrease the relative humidity beneath about 20%. The relative humidity eventually decreased beneath 10%.

The invention claimed is:

1. A fuel delivery system comprising:
a storage tank containing a fuel product;
a sump;
a pump having a first portion positioned in the sump and a second portion positioned in the storage tank; and
a water filtration system comprising:
a water filter positioned in the sump and configured to separate the fuel product into a filtered fuel product and a separated water product;
a fuel inlet passageway in fluid communication with the storage tank and the water filter via the pump to direct the fuel product to the water filter;
a fuel return passageway in fluid communication with the water filter and the storage tank to return the filtered fuel product to the storage tank;
a water removal passageway in fluid communication with the water filter to drain the separated water product from the water filter,
an inlet valve positioned along the fuel inlet passageway; and
a controller that opens the inlet valve at a predetermined start time outside of high-demand fuel dispensing hours.

2. The fuel delivery system of claim 1, wherein the fuel inlet passageway is coupled to the pump at a location upstream of a leak detector.

3. The fuel delivery system of claim 1, wherein the water removal passageway extends out of the sump to drain the separated water product continuously out of the sump.

4. The fuel delivery system of claim 1, further comprising a selective absorbent in fluid communication with the water removal passageway to remove oil from the separated water product.

5. The fuel delivery system of claim 1, wherein the fuel return passageway returns the filtered fuel product to the storage tank in a manner that promotes circulation in the storage tank.

6. A fuel delivery system comprising:
a storage tank containing a fuel product;
a sump;
a pump having a first portion positioned in the sump and a second portion positioned in the storage tank; and
a water filtration system comprising:
a water filter positioned in the sump and configured to separate the fuel product into a filtered fuel product and a separated water product;
a fuel inlet passageway in fluid communication with the storage tank and the water filter via the pump to direct the fuel product to the water filter;
a fuel return passageway in fluid communication with the water filter and the storage tank to return the filtered fuel product to the storage tank;
a water removal passageway in fluid communication with the water filter to drain the separated water product from the water filter;
a drain valve positioned along the water removal passageway;
a high-level water sensor positioned in the water filter; and
a controller that opens the drain valve when the high-level water sensor detects water in the water filter.

7. The fuel delivery system of claim 6, further comprising a low-level water sensor positioned in the water filter, wherein the controller closes the drain valve when the low-level water sensor does not detect water in the water filter.

8. The fuel delivery system of claim 6, wherein the high-level water sensor is positioned beneath an entry into the fuel return passageway.

9. A fuel delivery system comprising:
a storage tank containing a fuel product;
a sump;
a pump having a first portion positioned in the sump and a second portion positioned in the storage tank; and
a water filtration system comprising:
a water filter positioned in the sump and configured to separate the fuel product into a filtered fuel product and a separated water product;

a fuel inlet passageway in fluid communication with the storage tank and the water filter via the pump to direct the fuel product to the water filter;

a fuel return passageway in fluid communication with the water filter and the storage tank to return the filtered fuel product to the storage tank;

a water removal passageway in fluid communication with the water filter to drain the separated water product from the water filter, wherein the water removal passageway extends to a second storage tank positioned in the sump to drain the separated water product into the second storage tank.

10. The fuel delivery system of claim 9, further comprising:

a high-level water sensor positioned in the second storage tank; and a controller that sends a communication requiring the second storage tank to be emptied when the high-level water sensor detects water in the second storage tank.

11. A fuel delivery system comprising:

a storage tank containing a fuel product;

a dispenser;

a water filter;

a fuel uptake line in fluid communication with the storage tank and the dispenser to deliver the fuel product to the dispenser;

a filtration uptake line in fluid communication with the storage tank and the water filter to deliver the fuel product to the water filter, the water filter being configured to separate the fuel product into a filtered fuel product and a separated water product, wherein an inlet to the filtration uptake line is positioned closer to a bottom surface of the storage tank than an inlet to the fuel uptake line;

a fuel return passageway in fluid communication with the water filter and the storage tank to return the filtered fuel product to the storage tank; and a water removal passageway in fluid communication with the water filter to drain the separated water product from the water filter.

12. The fuel delivery system of claim 11, further comprising:

a pump positioned along the fuel uptake line; and an eductor positioned along the filtration uptake line.

* * * * *